US007012129B2

(12) United States Patent
Vahlne et al.

(10) Patent No.: US 7,012,129 B2
(45) Date of Patent: Mar. 14, 2006

(54) ANTIVIRAL COMPOSITION COMPRISING GLYCINE AMIDE

(75) Inventors: Anders Vahlne, Stockholm (SE); Laura Goobar-Larsson, Stockholm (SE)

(73) Assignee: Tripep AB, Huddinge (SE)

( * ) Notice: Subject to any disclaimer, the term of this patent is extended or adjusted under 35 U.S.C. 154(b) by 168 days.

(21) Appl. No.: 10/406,012

(22) Filed: Apr. 1, 2003
(Under 37 CFR 1.47)

(65) Prior Publication Data

US 2004/0038908 A1 Feb. 26, 2004

Related U.S. Application Data

(63) Continuation of application No. 10/235,158, filed on Sep. 3, 2002, now abandoned.

(60) Provisional application No. 60/323,650, filed on Sep. 19, 2001.

(51) Int. Cl.
*A61K 38/00* (2006.01)
(52) U.S. Cl. .................. 530/332; 424/451; 424/463; 424/474; 424/477; 424/278.1
(58) Field of Classification Search ................ 530/332; 424/451, 463, 474, 477, 278.1
See application file for complete search history.

(56) References Cited

U.S. PATENT DOCUMENTS

| 4,215,112 A | 7/1980 | Goldstein et al. |
|---|---|---|
| 4,528,133 A | 7/1985 | Kasafirek et al. |
| 4,612,337 A | 9/1986 | Fox et al. |
| 4,658,013 A | 4/1987 | Morgan |
| 4,818,540 A | 4/1989 | Chinen et al. |
| 4,857,538 A | 8/1989 | Kashman et al. |
| 4,950,647 A | 8/1990 | Robins et al. |
| 5,336,758 A | 8/1994 | Berzofsky et al. |
| 5,346,989 A | 9/1994 | Vahlne et al. |
| 5,449,752 A | 9/1995 | Fujii et al. |
| 5,470,951 A | 11/1995 | Roberts |
| 5,478,810 A | 12/1995 | Stuber et al. |
| 5,571,892 A | 11/1996 | Fujii et al. |
| 5,607,858 A | 3/1997 | Stuber et al. |
| 5,627,035 A | 5/1997 | Vahlne et al. |
| 5,710,128 A | 1/1998 | Fujii et al. |
| 5,744,368 A | 4/1998 | Goldgaber et al. |
| 5,770,620 A | 6/1998 | Mjalli et al. |
| 5,776,899 A | 7/1998 | Matsumoto et al. |
| 5,817,626 A | 10/1998 | Findeis et al. |
| 5,830,910 A | 11/1998 | Mattson |
| 5,830,994 A | 11/1998 | D'Hinterland et al. |
| 5,843,904 A | 12/1998 | Bemis et al. |
| 5,843,995 A | 12/1998 | Rana et al. |
| 5,846,714 A | 12/1998 | Haskill et al. |
| 5,854,204 A | 12/1998 | Findeis et al. |
| 5,856,122 A | 1/1999 | Read et al. |
| 5,858,979 A | 1/1999 | Kakkar et al. |
| 5,872,210 A | 2/1999 | Medabalimi |
| 5,886,025 A | 3/1999 | Pinney |
| 5,932,550 A | 8/1999 | Kato et al. |
| 6,184,210 B1 | 2/2001 | Keanna et al. |
| 6,242,416 B1 | 6/2001 | Gilchrest et al. |
| 6,258,932 B1 | 7/2001 | Vahlne |
| 6,455,670 B1 | 9/2002 | van der Spoel et al. |
| 2002/0091086 A1 | 7/2002 | Vahlne |

FOREIGN PATENT DOCUMENTS

| EP | 0 421 074 A1 | 4/1991 |
|---|---|---|
| EP | 0 894 855 A2 | 2/1999 |
| EP | 0 900 566 A1 | 3/1999 |
| FR | 2 668 488 A1 | 4/1992 |
| GB | 1063727 | 3/1967 |
| WO | WO 90/04390 | 5/1990 |
| WO | WO 92/20795 | 11/1992 |
| WO | WO 96/27386 | 9/1996 |
| WO | WO 96/28162 | 9/1996 |
| WO | WO 96/35714 | 11/1996 |
| WO | WO 98/09985 | 3/1998 |
| WO | WO 98/35062 | 8/1998 |
| WO | WO 99/09056 | 2/1999 |
| WO | WO 99/09985 | 3/1999 |
| WO | WO 00/09158 | 2/2000 |
| WO | WO 01/10456 | 2/2001 |
| WO | WO 01/10457 | 2/2001 |

OTHER PUBLICATIONS

Bachem catalog, Bachem Bioscience Inc. 1993, pp. 263 and 632.*
Abdel-Meguid et al., "An orally bioavailable HIV-1 protease inhibitor containing an imidazole-derived peptide bond replacement: Crystallographic and pharmacokinetic analysis," *Biochemistry*, 33(39):11671-11677 (1994).
Allured et al., "Structure of exotoxin A of pseudomonas aeruginosa at 3.0- angstrom resolution," *Proc Natl Acad Sci USA*, 83(5):1320-1324 (1986).
Armstrong et al., "A phase 1 study of chemically synthesized verotoxin (Shiga-like toxin) Pk-trisaccharide receptors attached to chromosorb for preventing hemolytic-uremic syndrome," *J. Infectious Diseases*,J14 171:1042-1045 (1995).
Armstrong and Peppler, "Maintenance of biological activity of pertussis toxin radioiodinated while bound to fetuin-agarose," *Infection & Immunity*, 55(5):1294-1299 (1987).

(Continued)

*Primary Examiner*—Jeffrey Stucker
(74) *Attorney, Agent, or Firm*—Knobbe, Martens, Olson & Bear, LLP

(57) ABSTRACT

Embodiments relate to the discovery that certain tripeptide amides and glycine amide can be used to inhibit viral infection, including human immunodeficiency virus (HIV) infection. More specifically, medicaments comprising said tripeptide amides and/or glycine amide and methods of using said compounds for the prevention and treatment of viral infection, such as HIV infection, are provided.

19 Claims, 4 Drawing Sheets

OTHER PUBLICATIONS

Ashkenazi et al., "Safety and antitumor activity of recombinant soluble Apo2 ligand," *J Clinical Investigation*, 104(2):155-162 (1999).

Bai et al., "Characterization of the interaction of cryptophycin 1 with tubulin: binding in the vinca domain, competitive inhibition of dolastatin 10 binding, and an unusual aggregation reaction," *Cancer Research*, 56:4398-4406 (1996).

Barger et al., "Tumor necrosis factors α and β protect neurons against amyloid β-peptide toxicity: Evidence for involvement of a κB-binding factor and attenuation of peroxide and Ca2+ accumulation," *Proc Natl Acad Sci USA*, 92:9328-9332 (1995).

Brandhuber et al., "Mapping the enzymatic active site of pseudomonas aeruginosa exotoxin A," *Proteins*, 3(3):146-154 (1988).

Choe et al., "The crystal structure of diphtheria toxin," *Nature*, 357(6375):216-222 (1992).

Chothia and Janin, "Principles of protein-protein recognition," Nature, 256(5520):705-708 (1975).

Conner et al., "Selective Proteasome Inhibition Attenuates Experimental Polyarthritis Via Inhibition of Nuclear Transcription Factor κB (NFκB) Activation," *Arthritis and Rheumatism, Abst. Suppl.*, 40(9), (1997).

Conner et al., "Proteasome Inhibition Attentuates Nitric Oxide Synthase Expression, VCAM-1 Transcription and the Development of Chronic Colitis," *Journal of Pharmacology and Exp Therapeutics*, 282(3):1615-1622, 1997.

Durso et al., "The antimitotic tripeptide hemiasterlin," *Proc Am Assoc Cancer Res Annual Meeting*, vol. 40, p. 286, Mar. 1999.

Erickson et al., "Design, activity, and 2.8 Å crystal structure of a C2 symmetric inhibior complexed to HIV-1 protease," Science, 249(4968):527-533 (1990).

Gamble et al., "Structure of the carboxyl-terminal dimerization domain of the HIV-1 capsid protein," *Science*, 278:849-853 (1997).

Glenner et al., "Alzheimer's disease: initial report of the purification and characterization of a novel cerebrovascular amyloid protein," *Biochem Biophys Res Commun*, 120(3):885-890 (1984).

Grannelli-Piperno, et al., "Efficient Interaction of HIV-1 with Purified Dendritic Cells via multiple chemokine Coreceptors," *J Exp Med*, 184:2433-2438 (1996).

Hall et al., "Substituted 4-hydroxyproline di- and tripeptides as cytotoxic agents," *Amino Acids*, 16(1):79-89 (1999).

Head et al., "Preparation of VT1 and VT2 hybrid toxins from their purified dissociated subunits," *J Biol Chem*, 266(6):3617-3621 (1991).

Henderson et al., "Gag proteins of the highly replicative MN strain of human immunodeficiency virus type 1: postranslational modifications, proteolytic processing, and complete amino acid sequences," *Journal of Virology*, 66(4):1856-1865 (1992).

Hewlett et al., "Induction of a novel morphological response in Chinese hamster ovary cells by pertussis toxin," Infect. Immun., 40(3):1198-1203 (1983).

Hilbich et al., "Substitutions of hydrophobic amino acids reduce the amyloidogenicity of alzheimer's disease βA4 peptides," *J Mol Biol*, 228:460-473 (1992).

Huang et al., "The role of DNA in the mechanism of NFκB dimer formation: crystal structures of the dimerization domains of the p50 and p65 subunits," Structure, 5(11):1427-1436 (1997).

Hwang et al., "Identification of the envelope V3 loop as the primary determinant of cell tropism in HIV-1," *Science*, 253:71-74 (1991).

Ito et al., "Isolation and some properties of A and B subunits of Vero toxin 2 and in vitro formation of hybrid toxins between subunits of Vero toxin 1 and Vero toxin 2 from *Escherichia coli* O157:H7," *Microb Pathog*, 5(3):189-195 (1988).

Jarret and Lansbury, "Seeding 'One-dimensional crystallization' of amyloid: a pathogenic mechanism in alzheimer's disease and scrapie?" *Cell*, 73:1055-1058 (1993).

Kowalski et al., "Functional regions of the envelope glycoprotein of human immunodeficiency virus type I," *Science*, 237:1351-1355 (1987).

Lassila et al., "A Role for Lys-His-Gly-NH2 in Avian and Murine B Cell Development," *Cell. Immun.*, 122:319-328, (1989).

Latimer et al., "The N-terminal domain of IκBα Masks the nuclear localization signal(s) of p50 and c-Rel homodimers," Mol. Cell Biol., 18(5):2640 (1998).

LeVine, "Thioflavine T interaction with synthetic Alzheimer's disease beta-amyloid peptides: detection of amyloid aggregation in solution," *Protein Science*, 2(3):404-410 (1993).

Lingwood, "Role of verotoxin receptors in pathogenesis," *Trends in Microbiology*, 4(4):147-153 (1996).

Lobet et al., "Site-specific alterations in the B oligomer that affect receptor-binding activities and mitogenicity of pertussis toxin," *J Exp Med*, 177(1):79-87 (1993).

Loosmore et al., "Characterization of pertussis toxin analogs containing mutations in B-oligomer subunits," *Infect Immun*, 61(6):2316-2324 (1993).

Louis et al., "Hydrophilic peptides derived from the transframe region of GaPol inhibit the HIV-1 protease," *Biochemistry*, 37(8):2105-2110 (1998).

Maldonado et al., "Experimental chemotherapy with combinations of erogosterol biosynthesis inhibitors in murine models of chagas' disease," *Antimicrobial Agents and Chemotherapy*, 37(6):1353-1359 (1993).

Malek et al., "IκBα Functions through direct contacts with the nuclear localization signals and the DNA binding sequences of NF-αB," J. Biol. Chem., 273(39):25427-25435 (1998).

Martin, "Fast-acting slow viruses," *Nature*, 345:572-573 (1990).

Masters et al., "Amyloid plaque core protein in Alzheimer disease and Down syndrome," *Proc Natl Acad Sci USA*, 82(12):4245-4249 (1985).

Memar O. et al., "Antiviral Agents in Dermatology; Current Status and Future Prospects," *Internation Journal of Dermatology*, 34(9):597-606 (1995).

Merritt, et al., "Surprising leads for a cholera toxin receptor-binding antagonist: crystallographic studies of CTB mutants," Structure, 3(6):561-570 (1995).

Miller, et al., "Antiviral activity of carbobenzoxy Di- and Tripeptides on measles virus," *Applied Microbiology*, 16(10):1489-1496 (1968).

Monks et al., "Feasibility of a high-flux anticancer drug screen using a diverse panel of cultured human tumor cell lines," *J. National Cancer Institute*, 83(11):757-766 (1991).

Mukaida, et al., "Novel insight into molecular mechanism of endotoxin shock: biochemical analysis of LPS receptor signaling in a cell-free system targeting NF-κB and regulation of cytokine production/action through $\beta_2$ integrin in vivo," Journal of Leukocyte Biology, 59(2):145-151 (1996).

Niedrig et al., "Inhibition of infectious human immunodeficiency virus type 1 particle formation by Gag protein derived peptides," *Journal of General Virology*, 75:1469-1474 (1994).

Owellen et al., "Inhibition of tubulin-microtubule polymerization by drugs of the Vinca alkaloid class," *Cancer Res.*, 36(4):1499 (1976).

Palker et al., "Type-specific neutralization of the human immunodeficiency virus with antibodies to env-encoded synthetic peptides," Proc. Natl. Acad. Sci. USA, 85(6):1932-1936 (1988).

Prusiner, "Some speculations about prions, amyloid, and Alzheimer's disease," *N. Engl. J. Med.*, 310(10): 661-663 (1984).

Prusiner, "Molecular biology of prion diseases," *Science*, 252(5012):1515-1522 (1991).

Rao et al., "3'-(p-azidobenzamido)taxol photolabels the N-terminal 31 amino acids of beta-tubulin," *J. Biol. Chem.*, 269(5):3132-3134 (1994).

Richards, "Inhibition of the aspartic proteinase from HIV-2," *FEBS Letters*, 253(1,2):214-216 (1989).

Sawada et al., "Identification of the fragment photoaffinity-labeled with azidodansyl-rhizoxin as Met-363-Lys0379 on beta-tubulin," *Biochem. Pharmacol.*, 45(7):1387-1394 (1993).

Sheha et al., "Synthesis of di- and tripeptide analogues containing α-ketoamide as a new core structure for inhibition of HIV-1 protease," Eur. J. Med. Chem., 35(10):887-894 (2000).

Sigma, Peptide and Amino Acid Catalog, p. 27 and p. 70, Copyright 1995-96.

Sixma et al., "Comparison of the B-pentamers of heat-labile enterotoxin and verotoxin-1: two structures with remarkable similarity and dissimilarity," *Biochemistry*, 32(1):191-198 (1993).

Sixma et al., "Refined structure of *Escherichia coli* heat-labile enterotoxin, a close relative of cholera toxin," *J. Mol. Biol.*, 230(3):890-918 (1993).

Sheppard, R. C., Peptide synthesis, solid phase. In: Molecular Biology and Biotechnology: a comprehensive desk reference. Ed: Meyers R.A. 1995, VCH Publisheres Inc., New York, NY.

Stein et al., "Crystal structure of the cell-binding B oligomer of verotoxin-1 from *E. coli*," *Nature*, 355:748-750 (1992).

Su et al., "The nontoxic tripeptide glycyl-prolyl-glycine amide inhibits the replication of human immunodeficiency virus type 1," *Journal of Human Virology*, 4(1):1-7 (2001).

Su et al., "The tripeptide glycyl-prolyl-glycine amide does not affect the early steps of the human immunodeficiency virus type 1 replication," *Journal of Human Virology*, 4(1):8-15 (2001).

Vahine, "Protein Polymerization Inhibitors and Methods of Use," U.S. Appl. No. 10/072,783 filed Feb. 8, 2002.

Van Der Spoel et al., "Tripeptide Amides that Block Viral Infectivity and Methods of use Thereof," U.S. Appl. No. 09/938,806, filed Aug. 24, 2001.

Van Der Spoel et al., "Pentamer Peptide Amide, ALGPGNH2, which Inhibits Viral Infectivity and Methods of Use Thereof," U.S. Appl. No. 10/217,933, filed Aug. 12, 2002.

Goobar-Larsson et al., "Molecules that Block Viral Infectivity and Methods of Use Thereof," U.S. Appl. No. 10/217,933, filed Sep. 3, 2002.

Bachem Catalog, Bachem Bioscience Inc. 1993, pp. 28, 29, 34, 145, 267, 332, 333, 457, 535, 536, 541, 546 and 553.

English translation of JP 05097789.

Certificate attesting the accuracy of the translation of JP 05097789.

\* cited by examiner

ANTIVIRAL COMPOSITION COMPRISING GLYCINE AMIDE

CROSS-REFERENCE TO RELATED APPLICATIONS

This application is a continuation of U.S. application Ser. No. 10/235,158, filed Sep. 03, 2002, now abandoned which claims priority to U.S. Provisional Application No. 60/323,650, filed Sep. 19, 2001. This application claims priority to U.S. application Ser. No. 10/235,158 and U.S. Provisional Application No. 60/323,650, both of which are hereby expressly incorporated by reference in their entireties.

FIELD OF THE INVENTION

The present invention relates to the discovery that certain tripeptide amides and glycine amide can be used to inhibit viral infection, including human immunodeficiency virus (HIV) infection. More specifically, medicaments comprising these tripeptide amides and glycine amide and methods of using said compounds for the prevention and treatment of viral infection, such as HIV infection, are provided.

BACKGROUND OF THE INVENTION

All viruses are composed of a protein shell surrounding a nucleic acid containing core. The protein shell directly surrounding the viral nucleic acid is called a capsid, whereas, the complete protein-nucleic acid complex having both the capsid and the nucleic acid is called a nucleocapsid. Arenaviruses, rotaviruses, orbiviruses, retroviruses (including lentiviruses), papillomaviruses, adenoviruses, herpesviruses, paramyxovirus, myxovirus, and hepadnaviruses all exhibit these general structural features. (*Virology*, Fields ed., third edition, Lippencott-Raven publishers, pp 1513, 1645, 1778, 2047, 2113, 2221, and 2717 (1996)).

The capsid is composed of many subunits (capsomeres) and capsomeres are formed from several homo- or heteropolymers of protein. The noncovalent bonds between capsomeres in a viral assembly are of the same sort that stabilize a folded protein domain. The interface between two subunits can look very much like a single domain, with amino acid side chains tightly packed against one another. A common feature to most of the virus structures analyzed is the way in which a polypeptide chain from one capsomere can extend under or over domains of neighboring capsomeres. These extended polypeptide arms intertwine with other polypeptide arms and help to stabilize the capsid by initiating hydrophobic interactions, hydrogen bonding, and salt bridges. Contacts between individual capsomeres, and for some viruses also contacts with core proteins, determine the overall capsid structure and if a number of identical capsomeres are involved, repeated contacts occur and the resulting structure is symmetrical. (Id. at 62).

Some simple viruses form spontaneously from their dissociated components while others require enzyme-catalyzed modifications of the capsomeres to trigger assembly. Viral self assembly is driven by the stability of the interactions between protein subunits under conditions that favor association. More complex viruses are often constructed from subassemblies that have undergone self assembly processes. (Id. at pp 62, 70, 1646 and 1888). Although the capsids of many viruses differ in protein composition, a general viral structural design has evolved characterized by polymerized capsomeres that, in turn, are composed of several homo- or hetero- polymers of protein.

HIV is the name given to a lentivirus that infects humans and that causes acquired immuno-deficiency syndrome (AIDS). The lentivirus isolates from humans are grouped into one of two types (HIV-1 and HIV-2) on the basis of serologic properties and sequence analysis of molecularly cloned viral genomes. Genetically distinct lentiviruses have been obtained from several non-human primate species including African green monkeys, sooty magabeys, mandrills, chimpanzees, and sykes. Collectively, the lentivirus isolates from non-human primates are called SIV. Sequence analysis reveals that the genomes of some SWV strains and HIV-1 and HIV-2 strains exhibit a high degree of homology. Further, electron microscopy reveals that the ultrastructure of HIV and SIV are similar in that both have virions about 110 nm in diameter with a cone-shaped nucleocapsid surrounded by a lipid bilayer membrane that contains envelope glycoprotein spikes. (Id. at pp.1882–1883).

HIV is a complex retrovirus containing at least seven genes. The viral structural genes, designated gag, pol, and env, respectively code for the viral core proteins, reverse transcriptase, and the viral glycoproteins of the viral envelope. The remaining HIV genes are accessory genes involved in viral replication. The gag and env genes encode polyproteins, i.e., the proteins synthesized from each of these genes are post-translationally cleaved into several smaller proteins.

Although the overall shape of HIV and SIV virions is spherical, the nucleocapsid is asymmetrical having a long dimension of about 100 nm, a wide free end about 40–60 nm, and a narrow end about 20 nm in width. The nucleocapsid within each mature virion is composed of two molecules of the viral single-stranded RNA genome encapsulated by proteins proteolytically processed from the Gag precursor polypeptide. Cleavage of the gag gene polyprotein Pr55$^{gag}$ by a viral coded protease (PR) produces mature capsid proteins. These gag gene products are the matrix protein (p17), that is thought to be located between the nucleocapsid and the virion envelope; the major capsid protein (p24), that forms the capsid shell; and the nucleocapsid protein (p9), that binds to the viral RNA genome. This proteolytic processing in infected cells is linked to virion morphogenesis. (Id. at pp 1886–1887).

The major capsid protein p24 (also called CA) contains about 240 amino acids and exhibits a molecular weight of 24–27 kD. The protein p24 self-associates to form dimers and oligomeric complexes as large as dodecamers. Genetic studies with mutations in the HIV-1 gag polyprotein have identified several functional domains in the p24 protein including the C terminal half of the molecule and a major homology region (MHR) spanning 20 amino acids that is conserved in the p24 proteins of diverse retroviruses. These mutations appear to affect precursor nucleocapsid assembly. (Id. at pp 1888–1889).

Since the discovery of HIV-1 as the etiologic agent of AIDS, significant progress has been made in understanding the mechanisms by which the virus causes disease. While many diagnostic tests have been developed, progress in HIV vaccine therapy has been slow largely due to the heterogeneous nature of the virus and the lack of suitable animal models. (See, e.g., Martin, *Nature*, 345:572–573 (1990)).

A variety of pharmaceutical agents have been used in attempts to treat AIDS. Many, if not all, of these drugs, however, create serious side effects that greatly limit their usefulness as therapeutic agents. HIV reverse transcriptase is one drug target because of its crucial role in viral replication. Several nucleoside derivatives have been found to inhibit HIV reverse transcriptase including azidothymidine (AZT, zidovudine®). AZT causes serious side effects such that many patients cannot tolerate its administration. Other nucleoside analogs that inhibit HIV reverse transcriptase have been found to cause greater side effects than AZT. Another drug target is the HIV protease (PR) crucial to virus development. PR is an aspartic protease and can be inhibited by synthetic compounds. (Richards, *FEBS Lett.*, 253:214–216 (1989)). Protease inhibitors inhibit the growth of HIV more effectively than reverse transcriptase inhibitors but prolonged therapy has been associated with metabolic diseases such as lipodystrophy, hyperlipidemia, and insulin resistance.

Additionally, HIV quickly develops resistance to nucleoside/nucleotide analogue reverse transcriptase inhibitors and protease inhibitors. This resistance can also spread between patients. Studies have shown, for example, that one tenth of the individuals recently infected by HIV already have developed resistance to AZT, probably because they were infected by a person that at the time of transmission carried a virus that was resistant to AZT.

It would be useful in the treatment and prevention of viral infections, including HIV and SIV, to have specific and selective therapeutic agents that cause few, if any, side effects.

SUMMARY OF THE INVENTION

The present invention is related to molecules that inhibit viral infectivity, specifically replication of Human Imnmunodeficiency Virus (HIV). It was discovered that certain tripeptides and the amino acid glycine, with their carboxyl terminus hydroxyl group replaced with an amide group, have an inhibiting effect on the replication of viruses, such as HIV. It is contemplated that these molecules inhibit viral replication by affecting protein-protein interactions during capsid assembly and/or by interfering with virus budding.

In addition to glycine amide (G-$NH_2$), the tripeptide amides AIG-$NH_2$, GFG-$NH_2$, GWG-$NH_2$, FLG-$NH_2$, GYG-$NH_2$, APG-$NH_2$, GLG-$NH_2$, and α-t-butylglycine-PG-$NH_2$ are the preferred species. These molecules and peptidomimetics resembling their structure (collectively referred to as "peptide agents") are used in a monomeric or multimeric form. Glycine amide and the tripeptide amides (i.e., peptide agents) are suitable for therapeutic and prophylactic application in mammals, including man, suffering from viral infection. Glycine amide or any one of AIG-$NH_2$, GFG-$NH_2$, GWG-$NH_2$, FLG-$NH_2$, GYG-$NH_2$, APG-$NH_2$, GLG-$NH_2$, and α-t-butylglycine-PG-$NH_2$ can be administered individually or the molecules can be provided in any combination (e.g., glycine amide can be provide with GLG-$NH_2$ or APG-$NH_2$ can be provided with GFG-$NH_2$, etc.)

In one embodiment, a composition for inhibiting viral replication in host cells infected with a virus has an effective amount of glycine amide and/or a peptide in amide form selected from the group of AIG-$NH_2$, GFG-$NH_2$, GWG-$NH_2$, FLG-$NH_2$, GYG-$NH_2$, APG-$NH_2$, GLG-$NH_2$, and α-t-butylglycine-PG-$NH_2$. In some embodiments, the compositions described above are joined to a support and in other embodiments, the compositions described above are incorporated into a pharmaceutical having a pharmaceutically acceptable carrier.

Methods of inhibiting viral replication in a host cell are also embodiments of the present invention. One approach, for example, involves administering to a cell an effective amount of glycine amide and/or a peptide in amide form selected from the group consisting of AIG-$NH_2$, GFG-$NH_2$, GWG-$NH_2$, FLG-$NH_2$, GYG-$NH_2$, APG-$NH_2$, GLG-$NH_2$, and α-t-butylglycine-PG-$NH_2$. The method described above can be supplemented with an antiviral treatment selected from the group consisting of nucleoside analogue reverse transcriptase inhibitors, nucleotide analogue reverse transcriptase inhibitors, non-nucleoside reverse transcriptase inhibitors, and protease inhibitors. The glycine amide and/or the tripeptide amide used in the method above can be joined to a support or can be administered in a pharmaceutical comprising a pharmaceutically acceptable carrier.

In another embodiment, a composition for inhibiting HIV replication in host cells includes an effective amount of glycine amide and/or a peptide in amide form selected from the group consisting of AIG-$NH_2$, GFG-$NH_2$, GWG-$NH_2$, FLG-$NH_2$, GYG-$NH_2$, APG-$NH_2$, GLG-$NH_2$, and α-t-butylglycine-PG-$NH_2$. In some embodiments, the glycine amide or the tripeptide amides are joined to a support and in other embodiments, these molecules are incorporated into a pharmaceutical comprising a pharmaceutically acceptable carrier.

In another method, an approach to inhibit HIV replication in host cells is provided, which involves administering to said cells an effective amount of glycine amide and/or a peptide in amide form selected from the group consisting of peptides of the formula AIG-$NH_2$, GFG-$NH_2$, GWG-$NH_2$, FLG-$NH_2$, GYG-$NH_2$, APG-$NH_2$, GLG-$NH_2$, and α-t-butylglycine-PG-$NH_2$. This method can also be supplemented by an antiviral treatment selected from the group consisting of nucleoside analogue reverse transcriptase inhibitors, nucleotide analogue reverse transcriptase inhibitors, non-nucleoside reverse transcriptase inhibitors, and protease inhibitors. Further, the glycine amide and/or tripeptide amide used in this method can be joined to a support or can be administered in a pharmaceutical comprising a pharmaceutically acceptable carrier.

In another method, an approach for interrupting viral capsid assembly is provided. This approach involves contacting a cell with an effective amount of glycine amide and/or a peptide in amide form selected from the group consisting of peptides of the formula AIG-$NH_2$, GFG-$NH_2$, GWG-$NH_2$, FLG-$NH_2$, GYG-$NH_2$, APG-$NH_2$, GLG-$NH_2$, and α-t-butylglycine-PG-$NH_2$. The glycine amide and/or the tripeptide amide can be joined to a support or incorporated in a pharmaceutical.

In another method, an approach for inhibiting proper viral budding is provided. This approach involves contacting a cell with an effective amount of glycine amide and/or a peptide in amide form selected from the group consisting of peptides of the formula AIG-$NH_2$, GFG-$NH_2$, GWG-$NH_2$, FLG-$NH_2$, GYG-$NH_2$, APG-$NH_2$, GLG-$NH_2$, and α-t-butylglycine-PG-$NH_2$. The glycine amide and/or the tripeptide amide can be joined to a support or incorporated in a pharmaceutical.

In still another method, an approach for interrupting HIV capsid assembly is provided. This approach also involves contacting a cell with an effective amount of glycine amide and/or a peptide in amide form selected from the group consisting of peptides of the formula AIG-$NH_2$, GFG-$NH_2$, GWG-$NH_2$, FLG-$NH_2$, GYG-$NH_2$, APG-$NH_2$, GLG-$NH_2$, and α-t-butylglycine-PG-$NH_2$. The glycine amide and/or the tripeptide amide of this method can be joined to a support or incorporated in a pharmaceutical.

In still another method, an approach for inhibiting proper HIV budding is provided. This approach also involves contacting a cell with an effective amount of glycine amide and/or a peptide in amide form selected from the group consisting of peptides of the formula AIG-$NH_2$, GFG-$NH_2$, GWG-$NH_2$, FLG-$NH_2$, GYG-$NH_2$, APG-$NH_2$, GLG-$NH_2$, and α-t-butylglycine-PG-NH$_2$. The glycine amide and/or the tripeptide amide of this method can be joined to a support or incorporated in a pharmaceutical.

Methods of identification of peptide agents that inhibit viral replication, specifically HIV replication are also provided. By one method, for example, a peptide agent for incorporation into an anti-viral pharmaceutical is identified by contacting a plurality of cells infected with a virus with an effective amount of a peptide agent, analyzing the virus for incomplete capsid formation or impaired viral budding, and selecting the peptide agent that induces incomplete capsid formation or induces impaired viral budding. This method can involve an analysis of capsid formation or viral budding that employs microscopy (e.g., electron microscopy) and the virus can be selected from the group consisting of HIV-1, HIV-2, and SWV. Further, the peptide agent identified can be selected from the group consisting of glycine amide, a tripeptide amide, and a peptidomimetic resembling glycine amide or a tripeptide amide. For example, the peptide agent above can be selected from the group consisting of glycine amide, AIG-NH$_2$, GFG-NH$_2$, GWG-NH$_2$, FLG-NH$_2$, GYG-NH$_2$, APG-NH$_2$, GLG-NH$_2$, and α-t-butylglycine-PG-NH$_2$.

In another embodiment, a method of identifying a peptide agent that binds to a viral protein is provided. Some aspects of this method involve providing a viral protein, contacting the viral protein with an effective amount of a peptide agent, and detecting the formation of a complex comprising the viral protein and the peptide agent. Some methods use a viral protein that is from a virus selected from the group consisting of HIV-1, HIV-2, and SIV. Further, in some embodiments, the peptide agent is selected from the group consisting of glycine amide, a tripeptide amide and a peptidomimetic resembling glycine amide or a tripeptide amide. Desirably, the method above employs glycine amide and/or a peptide agent selected from the group consisting of AIG-NH$_2$, GFG-NF$_2$, GWG-NH$_2$, FLG-NH$_2$, GYG-NH$_2$, APG-NH$_2$, GLG-NH$_2$, and α-t-butylglycine-PG-NH$_2$. Additionally, a method of making a pharmaceutical is provided in which the peptide agent identified by the methods above are incorporated in a pharmaceutical.

Another approach to making a pharmaceutical involves administering to a cell, especially a cell present in an animal such as a human, an effective amount of glycine amide or a peptide in amide form, described above, detecting an inhibition of viral replication in the cell, and incorporating the molecule that causes inhibition of viral replication into the pharmaceutical. This method can involve the use of glycine amide and/or a tripeptide amide selected from the group consisting of AIG-NH$_2$, GFG-NH$_2$, GWG-NH$_2$, FLG-NH$_2$, GYG-NH$_2$, APG-NH$_2$, GLG-NH$_2$, and α-t-butylglycine-PG-NH$_2$. Further, this method can be supplemented with administration of an antiviral compound selected from the group consisting of nucleoside analogue reverse transcriptase inhibitors, nucleotide analogue reverse transcriptase inhibitors, non-nucleoside reverse transcriptase inhibitors, and protease inhibitors into the pharmaceutical. Additionally, the method above can be supplemented by incorporating a carrier into the pharmaceutical.

DETAILED DESCRIPTION OF THE PREFERRED EMBODIMENT

Figure 1:
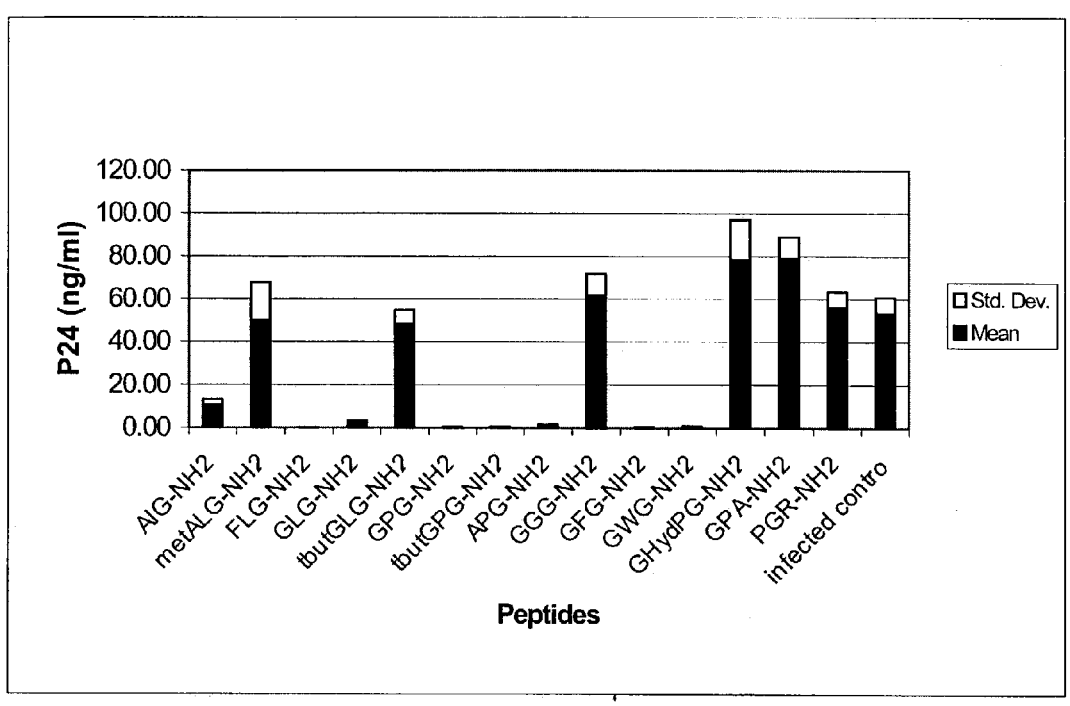
FIG. 1 shows the effect of GPG-NH$_2$ and ALG-NH$_2$ analogues on HIV-1 replication in H9 cells. The p24 levels in cell culture supernatants of HIV-1 infected cells, cultured in the presence or absence of tripeptide-amides, were measured at day 7 after infection by antigen capture-enzyme-linked immunosorbent assay (ELISA).

It has been discovered that glycine amide and certain tripeptide amides prevent and/or inhibit viral infection. Such amino acid or peptides are useful in the treatment of viral disease, particularly in HIV/AIDS afflicted subjects, and as preventive agents for patients at-risk of viral infection, particularly HIV infection, and for use with medical devices where the risk of exposure to virus is significant.

The disclosure below demonstrates that glycine amide and certain tripeptides in amide form, such as AIG-NH$_2$, GFG-NH$_2$, GWG-NH$_2$, FLG-NH$_2$, GYG-NH$_2$, APG-NH$_2$, GLG-NH$_2$, and α-t-butylglycine-PG-NH$_2$ inhibit the replication of viruses, for example HIV-1. Evidence of the inhibition of viral replication was found in viral infectivity assays that monitor the amount of capsid protein present in culture supernatant.

Several approaches to making biotechnological tools and pharmaceutical compositions comprising glycine amide and/or tripeptide amides and peptidomimetics that resemble these molecules (collectively referred to as "peptide agents") are given below. Preferred peptide agents are glycine and tripeptides with an amide group at their carboxy termini, and include the following: G-NH$_2$, AIG-NH$_2$, GFG-NH$_2$, GWG-NH$_2$, FLG-NH$_2$, GYG-NH$_2$, APG-NH$_2$, GLG-NH$_2$, and α-t-butylglycine-PG-NH$_2$. In some embodiments, the peptide agents are provided in monomeric form; in others, the peptide agents are provided in multimeric form or in multimerized form. Support-bound peptide agents are also used in several embodiments.

Pharmaceutical compositions comprising peptide agents are administered as therapeutics or prophylactics or both for the treatment and/or prevention of viral disease, particularly, HIV infection. In some embodiments, the pharmaceutical compositions comprising peptide agents are administered in combination with other antiviral treatments including nucleoside analogue reverse transcriptase inhibitors, nucleotide analogue reverse transcriptase inhibitors, non-nucleoside reverse transcriptase inhibitors, and protease inhibitors. These small molecules are resistant to acid hydrolysis. A significant amount of tripeptide amides, for example, is effectively delivered to blood, plasma, and organ tissue when administered to test subjects. The administration of large doses of small peptides to test subjects is relatively nontoxic. (See U.S. Pat. No. 6,258,932, which is herein expressly incorporated by reference in its entirety).

Additionally, several methods of identifying a peptide agent that inhibits or prevents viral replication or interrupts viral capsid assembly or both are provided. By one approach, an effective amount of a peptide agent is contacted with cells infected with a virus and the cells are analyzed for viral replication or the presence of viral products. Accordingly, a capsid protein (e.g., p24) is contacted with a peptide agent, for example a peptide in amide form, as described above, and a complex comprising the capsid protein (e.g., p24) bound with the peptide agent is identified.

The amide form of the molecules listed in TABLE 1 were tested. Many of these molecules were selected and synthesized because they are modifications of sequences that correspond to HIV and/or SIV viral proteins. The tripeptide amides of TABLE 1 were synthesized according to the method disclosed in EXAMPLE 1 below, but could of course be synthesized by any method known in the art. Glycine amide was purchased from Bachem, Switzerland (product No. 4025766), whereas Glycine-OH was purchased from Merck, Germany (product No. 14201-250). GPG-$NH_2$ was also purchased from Isochem, France.

TABLE 1

| | |
|---|---|
| GPG-$NH_2$: | glycyl-prolyl-glycine-amide |
| ALG-$NH_2$: | alanyl-leucyl-glycine-amide |
| GFG-$NH_2$: | glycyl-phenylalanyl-glycine-amide |
| GWG-$NH_2$: | glycyl-tryptophanyl-glycine-amide |
| FLG-$NH_2$: | fenylalanyl-leucyl-glycine-amide |
| GYG-$NH_2$: | glycyl-tyrosyl-glycine-amide |
| APG-$NH_2$: | alanyl-prolyl-glycine-amide |
| GLG-$NH_2$: | glycyl-leucyl-glycine-amide |
| α-t-butylglycine-PG-$NH_2$: | α-tertiary-butylglycine-prolyl-glycine-amide |
| LNF-$NH_2$: | leucyl-asparagyl-phenylalanine-amide |
| AIG-$NH_2$: | alanyl-isoleucyl-glycine-amide |
| GGG-$NH_2$: | glycyl-glycyl-glycine-amide |
| PGR-$NH_2$: | prolyl-glycine-arginine-amide |
| G-$NH_2$: | glycine amide |

EXAMPLE 1

In this example, the approaches used to obtain the tripeptide amides listed above are disclosed. The tripeptide amides were chemically synthesized with an automated peptide synthesizer (Syro, Multisyntech, Witten, Germany) largely according to the manufacturer's instructions. The synthesis was run using 9-fluorenylmethoxycarbonyl (Fmoc) protected amino acids (Milligen, Bedford, Mass.) according to standard protocols. The modified peptides were created by substituting an amino group for the hydroxyl residue normally present at the terminal carboxyl group of a peptide. That is, instead of a terminal COOH, the peptides were synthesized to have CO—$NH_2$. For example, in addition to glycine amide, the preferred tripeptide amides include AIG-$NH_2$, GFG-$NH_2$, GWG-$NH_2$, FLG-$NH_2$, GYG-$NH_2$, APG-$NH_2$, GLG-$NH_2$, and α-t-butylglycine-PG-$NH_2$. TABLE 2 lists the Fmoc amino acids used.

TABLE 2

Fmoc-Ala-OH
Fmoc-Arg(Pbf)-OH
Fmoc-Asn(Trt)-OH
Fmoc-Asp(OtBu)-OH
Fmoc-Cys(Trt)-OH
Fmoc-Glu(OtBu)-OH
Fmoc-Gln(Trt)-OH TABLE 2-continued Fmoc-Gly-OH
Fmoc-His(Trt)-OH
Fmoc-Ile-OH
Fmoc-Leu-OH
Fmoc-Lys(Boc)-OH
Fmoc-Met-OH
Fmoc-Phe-OH
Fmoc-Pro-OH
Fmoc-Ser(tBu)-OH
Fmoc-Thr(tBu)-OH
Fmoc-Trp(Boc)-OH
Fmoc-Tyr(tBu)-OH
Fmoc-Val-OH Rink amide MBHA resin (MultiSynTech, Witten, Germany) was used. Other reagents used to prepare the tripeptide amides included Acetic acid, Acetic anhydride, 2-(1H-Benzotriazole-1-yl)-1,1,3,3, tetramethyluronium tetrafluoroborate (TBTU), Diisopropylcarbodiimide (DIC), Dimethylformamide (DMF), Ethanedithiol (EDT), Ether, Ethyldiisopropylamine (DIPEA), Hydroxybenzotriazole (HOBt), Isopropanol, Lithium chloride, Methanol, Methylphenylsulfide, 1-Methyl-2-pyrrolidone (NMP), Piperidine, Pyridine, and Trifluoroacetic acid (TFA), all of which can be obtained from a variety of commercial suppliers.

The peptide synthesis was conducted as follows. The peptide sequences were entered into the synthesizer computer using the amino acid one letter codes and the correct sequences were verified by printing the entry. Next, the "cycle/chemfile relation", which specifies a chemfile for each coupling cycle, was initiated. Then the "chemfile editor" was initiated to study or modify the chemfiles, if necessary. A separate chemfile, which begins and ends with an Fmoc-deprotection step, was used for the first coupling cycle. The chemfiles used for the other coupling cycles only end with an Fmoc-deprotection. The chemfiles "swell single coupling DIC" (cycle 1) and "single coupling DIC" (cycle 2->) were used for standard syntheses.

Once the chemfiles and sequences had been entered, the "calculation" phase was begun. The resin loading equivalents (excess of amino acids) and resin amount weighed in each reactor was entered. A calculation report was printed. The resin in the plastic reactors was weighed and placed in the reaction block. A stock solution of HOBt in fresh DMF containing molecular sieve was prepared. The amino acids were weighed in 50 ml tubes and the HOBt solution above was used to dissolve the amino acids according to the calculation report. The molar relation between amino acid and HOBt was 1:1. The addition of HOBt prevented amino acid racemization. The tubes containing the amino acid solutions were then transferred to the building block box. The amino acid tubes were placed in alphabetical order from left to right according to the amino acid one-letter codes. The amino acid positions were also specified on the lid of the building block box and on the computer window of the SYRO II program.

Bottle 3 from the robot table was removed and washed with fresh DMF. Bottle 3 was used to dissolve DIC in DMF according to the calculation report then it was placed back into position on the robot table. DIC activates the carboxy group of the amino acids. Bottles 1 and/or 2 was used to prepare a 40% solution of piperidine in DMF according to the calculation report. It was not necessary to use fresh DMF for the piperidine solutions. The bottles (1 and 2) used for 40% piperidine were identified as such in the chemfiles. Piperidine cleaves the amino-protecting Fmoc group before each coupling. The chemfile used for coupling cycle 1 contained two piperidine cycles since an additional Fmoc group had to be removed from the resin before coupling of the first amino acid. The piperidine bottles were placed back into position on the robot table.

Under some circumstances, the double coupling of amino acids may be desired. Double coupling may result in more efficient synthesis of difficult sequences. The peptide quality may also be improved by increasing the coupling time and temperature or by increasing the Fmoc deprotection time. However, longer coupling times at higher temperatures may lead to unwanted side reactions and peptide degradation. Normally, the amino acids are coupled 40–60 minutes at 30° C. DIC is used as an activator in standard synthesis. During double coupling, DIC may be used as the only activator, or it may be used only in the first coupling in conjunction with a second activator system used in the second coupling. The use of different modes of activation may further increase the coupling efficacy. A second activator is TBTU together with DIPEA. However, this activator system has limited solubility. The use of double coupling and different activators is specified in the chemfiles. Solutions of DIPEA and TBTU in NMP are prepared in bottles 4 and 5 according to the calculation report. Before preparing the solutions, the bottles were washed with fresh NMP.

After each double coupling the unreacted free amino groups can be blocked by acetylation (capping). Acetylation prevents elongation of deletion peptides missing one or several amino acids. Also, the acetylated peptides are usually easily separated from the correct sequence since they appear late in reverse phase HPLC chromatogram due to their hydrophobicity. The acetylation solution 10% acetic anhydride/5% pyridine in DMF was prepared in bottle 7. Before preparing the acetylation solution, the bottle was washed with fresh DMF. Some crystals of lithium chloride were also added to the acetylation solution.

Next, the robotic arms and the brass rods were cleaned with a cloth that was wetted with isopropanol once the synthesizer had been turned off. Then the synthesizer was turned back on and the reagent bottles and building block box were placed in their fixed positions on the robot table. A 10 L brown glass bottle was then filled with DMF that was not older than two weeks. The gas tube (argon or nitrogen gas) was opened and the gas pressure was regulated with the pressure membrane regulator on the robot. The pressure was maintained at approximately 1 bar. The synthesis was started by clicking on "start synthesis" in the robot menu and the start and end positions were selected. During a large synthesis it may be necessary to fill the 10 L bottle with more DMF. The amount of DMF was checked regularly during the synthesis.

Once the synthesis had finished, a synthesis report was printed and analyzed to determine if all the couplings had completed. Next, a suitable cleavage chemfile was selected by clicking on "chemfile editor" in the tools menu. Then the "cycle/chemfile relation" was selected to specify the cleavage chemfile for coupling cycle 1. New glass tubes were placed in the cleavage box rack in the fume hood to the right of the synthesizer. The lid was placed on the cleavage box and the cleavage was initiated by clicking on "start synthesis" in the robot menu. Cycle 1 was selected for both start and end positions.

The cleavage solution was then prepared during the washing and transfer steps at the start of the cleavage chemfile. The cleavage mixture 2% water/2% EDTA/2% methylphenylsulfide/94% TFA was transferred to bottle 6 and placed in its fixed position on the robot table. All other bottles and the building block box were removed from the robot table. The standard "cleavage aut" chemfile contains several programmed stops to allow manual check of the cleavage line washings and also to allow change of glass tubes in the cleavage box before transfer of the cleavage mixture from the reactor block. The automatic dispensing of cleavage mixture was always monitored carefully. In the "cleavage aut" chemfile, cleavage mixture was added twice to reactors and transferred to the glass tubes. The total cleavage time was approximately 3 hours from addition of the first portion of cleavage mixture to the peptide reactors.

The tubes were stirred a few times after the cleavage mixture containing the peptide had been transferred to the glass tubes. After 3 hours, the cleavage mixtures were transferred from the glass tubes to 15 ml polypropylene centrifuge tubes with screw caps and labeled with peptide numbers. Approximately 6 ml of ether was dispensed with the automatic dispenser to the 15 ml tubes. The tubes were capped and gently mixed by hand.

The peptides were precipitated in the ether while the cleavage chemicals remained soluble. If a peptide did not precipitate immediately, it was kept in the fume hood for 1–3 days and the precipitate slowly developed. The peptides were then centrifuged for 5 min at 4000 rpm at 0° C. The ether was removed, fresh ether was added to the tubes and the peptide/ether solution was mixed gently again. A pasteur pipette was used when the peptide adhered to the bottom of the tube. After four such ether washings, the peptides were left to dry in the fume hood overnight.

After drying overnight, the dried peptides were resuspended in approximately 3–10 ml milli-Q water. A few drops of concentrated acetic acid was added to neutral and basic peptides that did not readily dissolve in pure water. The dissolved peptides were then transferred to 4 ml, 10 ml or 30 ml glass vials, the vials were covered with paper cloths held by rubber bands, and the vials were stored at −80° C. for at least 2 hours before lyophilization. All peptides were lyophilized and then dissolved at the appropriate concentration in Milli-Q water or phosphate-buffered saline (PBS). The peptides were next analyzed by reverse phase high performance liquid chromatography (RP-HPLC) using either a Chromolith Performance RP-18e 100-4.6 column (for analytical RP-HPLC) or a LiChrospher 100 RP-18e (10 $\mu$m) 250-10 (for preparative RP-HPLC).

RP-HPLC was performed as follows. The D-7000 HPLC system manager (HSM) was initiated, the purge valves of both pumps was opened and the pumps were purged. The purge flow was run for approximately one minute to flush the tubings. The purge flow was then stopped and the purge valves of the pumps were closed. In this system, pump A pumped water and pump B pumped the second solvent (usually methanol). Approximately, 0.25% trifluoroacetic acid was added to all solvents. Initially, a flow of 100% water was run through the column.

Next, a suitable method file and sample table was selected. The columns were equilibrated in water for at least 20 min or until the flow line was stable. For the analytical runs the following gradient was used: 0 min—100% water/0% methanol; 1.3 min—100% water/0% methanol; 6.3 min—0% water/100% methanol; 7.5 min—0% water/100% methanol; 8.8 min—100% water/0% methanol; and 10.0 min—100% water/0% methanol. Flow rate on the analytical column was 2 ml/min. and approximately 100 $\mu$l of sample was injected onto the column. Small columns were used for analytical HPLC and fractions were not collected.

For the preparative runs the following gradient was used: 0 min—100% water/0% methanol; 5.0 min—100% water/

0% methanol; 25.0 min—0% water/100% methanol; 30.0 min—0% water/100% methanol; 35.0 min—100% water/0% methanol; and 40.0 min—100% water/0% methanol. Flow rate for the preparative column was 6 ml/min. and approximately 1 ml of sample was injected onto the column. During preparative HPLC, the fraction collector was setup to collect one or several sample fractions. The rack parameters were carefully monitored to insure that the rack was compatible with the auto sampler. Once the HPLC runs were completed, that is, the peptide peak was identified and/or collected, 50% B (methanol) was run through the column (at least five column volumes) to strip the column. In the disclosure below, several assays that were used to identify the molecules that inhibit HIV-1 infection are described.

Small Molecules That Inhibit and/or Prevent HIV Replication and Infection

The tripeptide amides made according to EXAMPLE 1 were used in several HIV-1 infectivity assays to determine the ability of said tripeptide amides to inhibit HIV replication and/or infection. The efficiency of HIV-1 replication and status of HIV-1 infection was monitored by the concentration of p24 protein in the cell supernatant. (See e.g., U.S. Pat. Nos. 5,627,035 and 6,258,932, herein expressly incorporated by reference in their entireties, which describe similar HIV infectivity assays and others that can be used to analyze the tripeptide amides described herein). EXAMPLE 2 describes an approach that was used to screen several tripeptide amides and glycine amide for the ability to inhibit HIV-1 infection.

EXAMPLE 2

In this example, the methods that were used to analyze the ability of various tripeptide amides and glycine amide to inhibit HIV-1 replication are disclosed. In a first set of experiments, approximately $3 \times 10^5$ H9 cells were infected with HIV-1 (e.g., 50–100 $TCID_{50}$ per 300,000 H9 cells) to test the inhibitory effect of various tripeptide amides provided at 100 $\mu$M concentration. (See TABLE 3).

By one approach, virus was added at 50–100 $TCID_{50}$ to $3 \times 10^5$ H9 cells in a total volume of 500 $\mu$l containing RPMI 1640 medium supplemented with 10% (v/v) heat-inactivated fetal bovine serum (FBS), L-Glutamine, and Bensylpenicillin and Streptomycin (PS) (approximately 0.5 ml added to 500 ml RPMI medium), all available through LifeTechnology/GIBCO laboratories. This media is referred to as "RPMI++ media." Cell counting was accomplished using 0.2% tryphanblue dissolved in PBS and a Bürker cell counter chamber. The virus and cells were then mixed gently on a vortex and were incubated at 37° C. for one hour and thirty minutes. Next, the cells were pelleted at 1200 rpm for 7 minutes and the supernatant was discarded.

The cells were then resuspended in RPMI++ at a concentration of $3 \times 10^5$ cells per ml. One ml of cell suspetion was then added to each well in a 24-well plate containing the different tripeptide amides or glycine amide in 0.6 ml RPMI++. The final concentration of tripeptide amides or glycine amide was approximately 100 $\mu$M. Cells were then incubated at 37° C. in a 5% $CO_2$ enriched incubator. The medium was changed on day 4, 7, and finally day 11. The infection was stopped on day 11 or 14. During each media change, approximately 0.8 ml was replaced and 0.8 ml of the supernatant was transferred to a sterile 96 well plate and stored at −80° C. for p24 analysis.

The presence of p24 in the supernatants was determined using a p24 antigen detection method. Suitable p24 detection kits are commercially available (e.g., Abbott Laboratories, North Chicago, U.S.A.). By one approach, a capture-assay is employed, wherein the viral antigen is captured on a 96-well plate coated with a polyclonal anti-p24 rabbit serum (Swedish Institute for infectious disease control). The captured antigen is then detected with peroxidase conjugated anti-p24 mouse monoclonal antibodies. The conjugate is a pool of three different monoclonal antibodies. The analysis was performed with cell free supernatant directly from the cell culture or with supernatant that had been stored at −20° C. to −80° C.

Accordingly, a p24 standard was diluted (e.g., 4, 2, 1, 0.5, 0.25, 0.125, 0.0625 ng/ml) in RPMI++ media. The standard, recombinant HIV-1 LAI gag p24, was purchased from NIBSC, Centralized Facility for AIDS Reagent, MRC. (order no EVA620). In some cases, serial dilutions of the supernatants were made so as to more accurately detect p24 concentration. Coated plates (e.g., plates coated with a polyclonal anti-p24 rabbit serum) were washed 4 times with approximately 300–350 $\mu$l/well washing buffer (PBS with 0.05% Tween-20). The plates were inverted and tapped against absorbant paper after each wash to discard the superfluous washing buffer. Approximately, 100 $\mu$l of each sample and standard was added to individual wells on the plate. The plates were covered with tape and incubated at 37° C. for 2 hours or in the dark at room temperature over night.

Next, the plates were washed again as above. Approximately 100 $\mu$l/well of conjugate diluted in conjugate buffer (PBS with 0.5% Triton X-100, 0.5% Bovine Serum Albumin, 0.05% Tween-20, and 10% Fetal Bovine Serum). The plates were then covered with tape and incubated at 37° C. for 2 to 4 hours. The OPD substrate (ABBOTT) was then prepared by adding 1 tablet of OPD per 5 ml OPD substrate solution (12.8 mg OPD (o-phenylenediamine. 2 HCl) per tablet and 1 tablet was dissolved in 5 ml citrate-phosphate buffer containing 0.02% hydrogen peroxidase). The solution was kept in the dark until it was used. The conjugate bound plates were then washed as above and, after the final wash, 100 $\mu$of OPD substrate solution/well was added and the plates were incubated at room temperature for 30 minutes. The plates were protected from light during this period. The reaction was stopped with 100 $\mu$l 2.5M $H_2SO_4$/well and the absorbance was read at 490 nm and 650 nm As discussed in greater detail below, it was discovered that glycine amide and the tripeptide amides AIG-$NH_2$, GFG-$NH_2$, GWG-$NH_2$, FLG-$NH_2$, GYG-$NH_2$, APG-$NH_2$, GLG-$NH_2$, and α-t-butylglycine-PG-$NH_2$ inhibit HIV-1 infection.

The results of the experiments described in EXAMPLE 2 are shown in FIG. 1 and TABLE 3. Accordingly, several tripeptide amides were found to inhibit HIV-1 replication in H9 cells at a 100 $\mu$M concentration. Although some tripeptide amides had little affect on HIV infectivity (e.g., PGR-$NH_2$, OPA-$NH_2$, GhydPG-$NH_2$, GGG-$NH_2$, tbutGLG-$NH_2$, and metALG-$NH_2$) many tripeptide amides almost completely inhibited HIV replication (e.g., AIG-$NH_2$, FLG-$NH_2$, GLG-$NH_2$, GPG-$NH_2$, α-tbutGPG-$NH_2$, APG-$NH_2$, GFG-$NH_2$, and GWG-$NH_2$). In this experiment GPG-$NH_2$ was used as a positive control whereas GGG-$NH_2$ and PGR-$NH_2$, which were known to not inhibit HIV replication, were used as negative controls.

TABLE 3

| Peptides | p24 ng/ml Mean | Std. Dev. |
| --- | --- | --- |
| AIG-NH2 | 10.69 | 2.55 |
| metALG-NH2 | 49.80 | 17.88 |
| FLG-NH2 | 0.25 | 0.06 |
| GLG-NH2 | 2.71 | 0.75 |
| tbutGLG-NH2 | 48.26 | 6.51 |
| GPG-NH2 | 0.42 | 0.08 |
| tbutGPG-NH2 | 0.44 | 0.15 |
| APG-NH2 | 1.13 | 0.40 |
| GGG-NH2 | 61.82 | 9.95 |
| GFG-NH2 | 0.45 | 0.17 |
| GWG-NH2 | 0.61 | 0.29 |
| GHydPG-NH2 | 78.43 | 18.68 |
| GPA-NH2 | 78.88 | 10.17 |
| PGR-NH2 | 55.93 | 7.48 |
| infected control | 53.31 | 7.41 |

Figure 2:
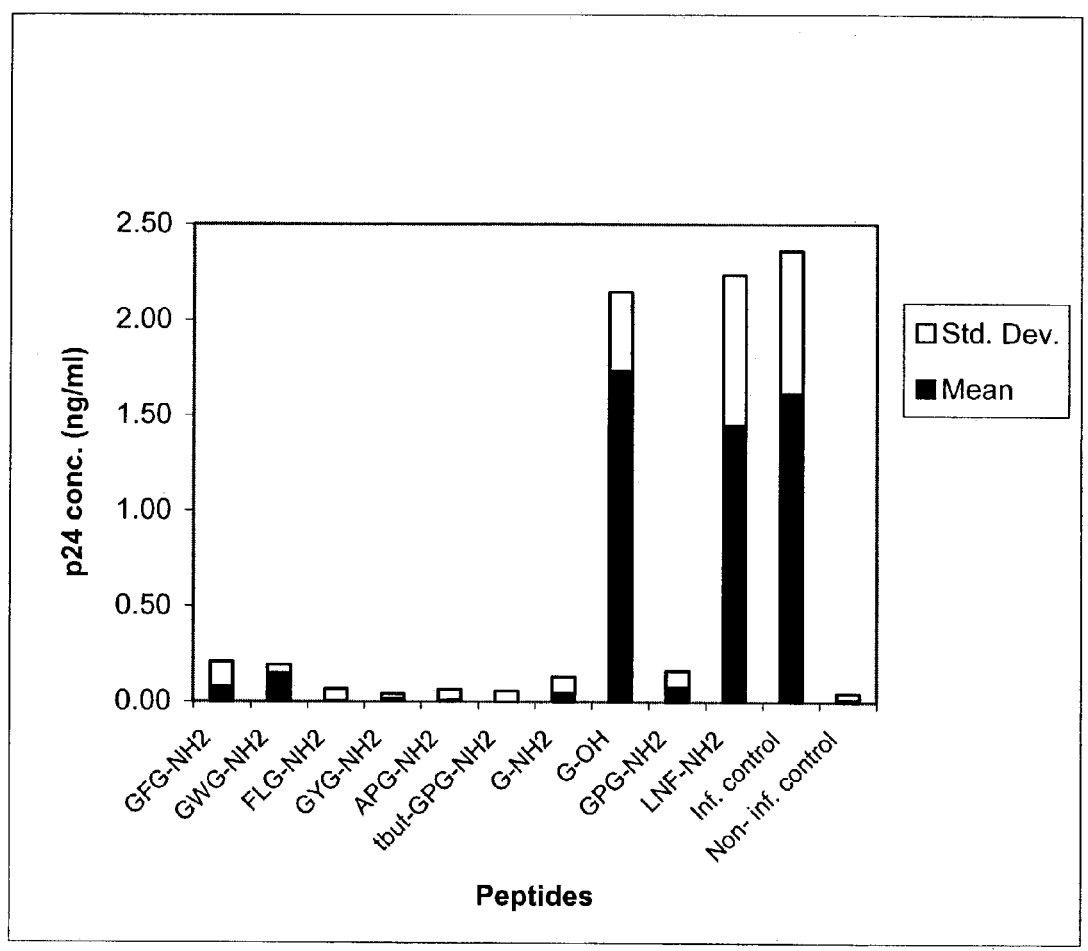
FIG. 2 shows the effect of glycine-amide and GPG-NH$_2$ and ALG-NH$_2$ analogues on HIV-1 replication in CEM cells. The p24 levels in cell culture supernatants of HIV-1 infected cells, cultured in the presence or absence of glycine amide or tripeptide-amides, were measured at day 11 after infection by antigen capture enzyme-linked immunosorbent assay (ELISA).

Several tripeptide amides and glycine amide were also evaluated for the ability to inhibit HIV replication in infected CEM cells, another T-cell line. The methods described in EXAMPLE 2 were used to conduct these experiments and FIG. 2 and TABLE 4 show the results. Again, GFG-NH$_2$, GWG-NH$_2$, FLG-NH$_2$, APG-NH$_2$, and tbutGPG-NH$_2$ were found to inhibit HIV-1 replication in infected cells at 100 $\mu$M concentration. Additionally, it was discovered that GYG-NH$_2$, and glycine amide inhibited HIV-1 replication in CEM cells. In contrast, an inhibition of HIV-1 replication was not observed for the natural amino acid glycine (G-OH). In this experiment LNF-NH$_2$ which was known to not inhibit HIV replication was used as negative control.

TABLE 4

| Peptides | Mean p24 (ng/ml) | Std. Dev. |
| --- | --- | --- |
| GFG-NH2 | 0.08 | 0.13 |
| GWG-NH2 | 0.15 | 0.04 |
| FLG-NH2 | 0.00 | 0.06 |
| GYG-NH2 | 0.02 | 0.02 |
| APG-NH2 | 0.01 | 0.05 |
| tbut-GPG-NH2 | −0.01 | 0.06 |
| G-NH2 | 0.04 | 0.09 |
| G-OH | 1.73 | 0.41 |
| GPG-NH2 | 0.07 | 0.09 |
| LNF-NH2 | 1.45 | 0.79 |
| Inf. control | 1.62 | 0.75 |
| Non-inf. control | 0.01 | 0.03 |

Figure 3:
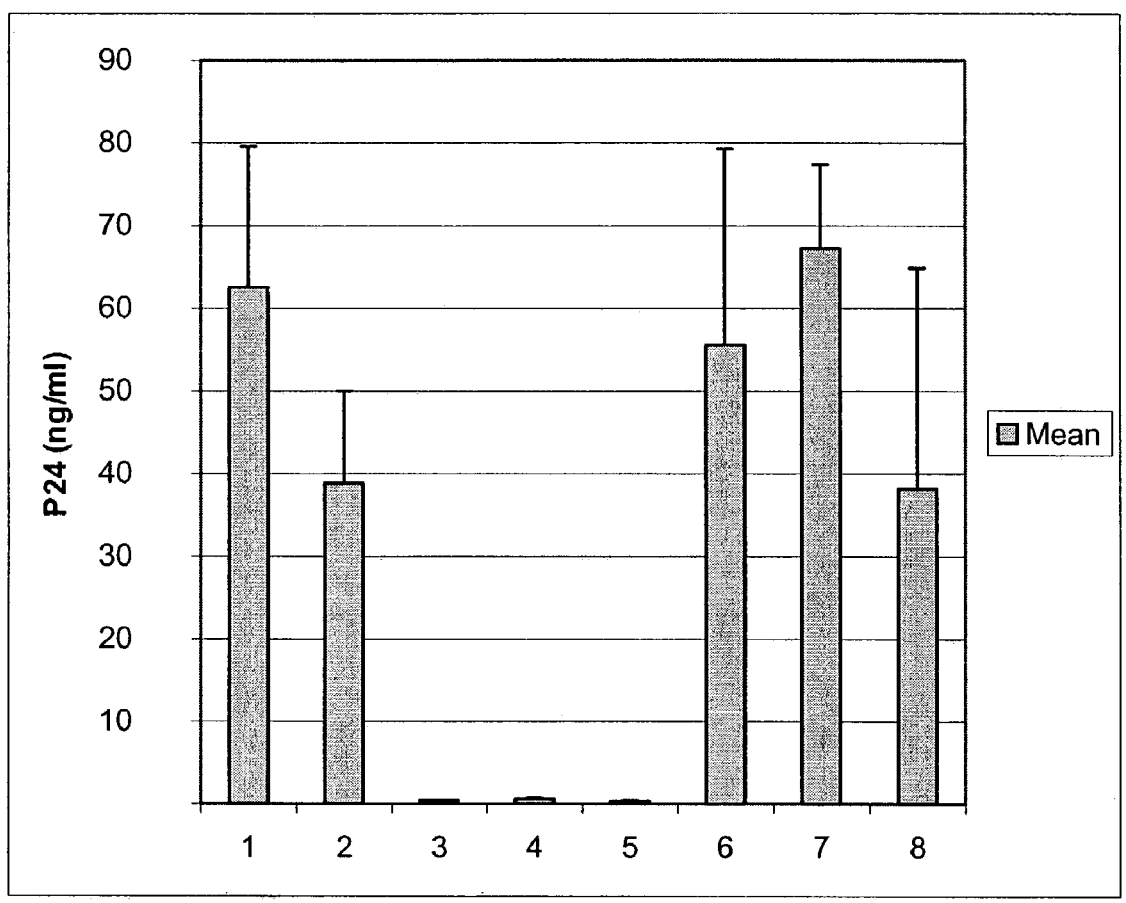
FIG. 3 shows H9 cells that were infected with 100 TCID$_{50}$ of HIV-1 in the presence or absence of 100 μM of GPG-NH$_2$ or one of its metabolites. Cell supernatants were harvested at day 11 post infection and the levels of p24 were measured by p24 antigen capture enzyme-linked immunosorbent assay (ELISA). 1=Infected control; 2=GPG-OH (negative control); 3=non-infected control; 4=GPG-NH$_2$; 5=G-NH$_2$; 6=GP-OH; 7=G-OH; 8=PG-NH$_2$.

In another set of experiments the ability of glycine amide to inhibit HIV replication was more closely analyzed. In these studies, HIV infected H9 cells were cultured in the presence 100 $\mu$M GPG-OH, GPG-NH$_2$, G-NH$_2$, GP-OH, G-OH, or PG-NH$_2$, as described previously (see EXAMPLE 2). As shown in FIG. 3, the amount of p24 detected in the culture supernatant of G-NH$_2$ treated cells (#5) at day 11 was almost identical to that found in the non-infected control (#3) and cells treated with GPG-NH$_2$ (#4). In contrast, HIV infected H9 cells treated with G-OH (#7) had considerable p24 present in the culture supernatant (approximately 65 ng/ml). These results provide additional evidence that glycine amide can be used to inhibit HIV infection or replication.

Figure 4:
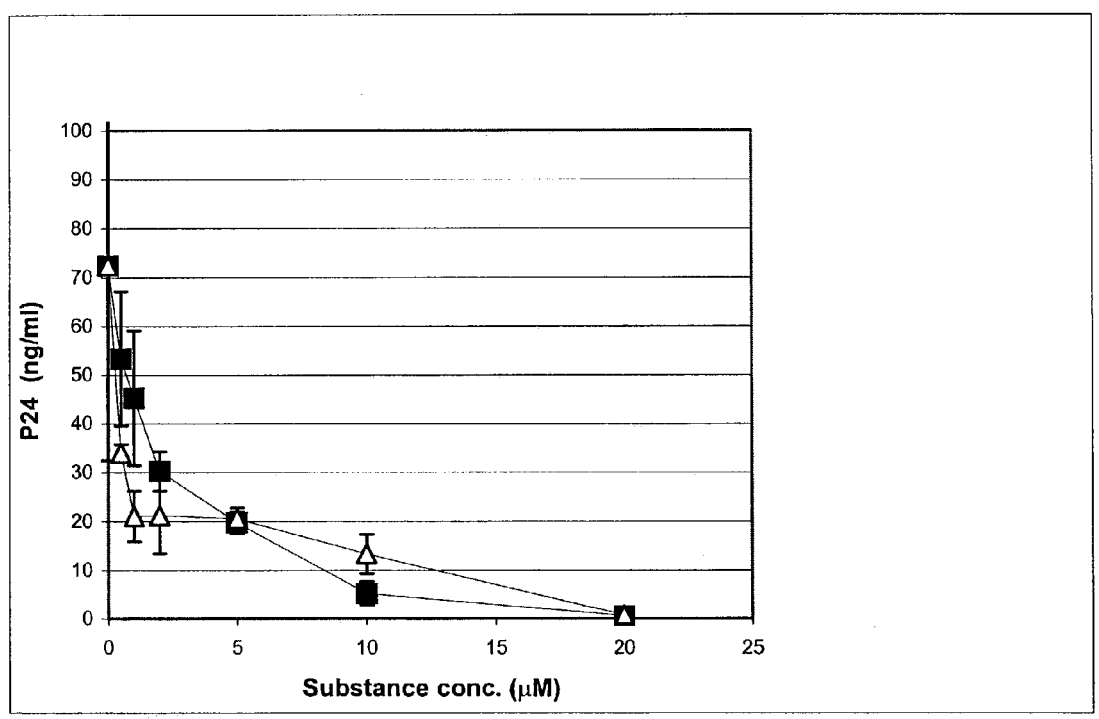
FIG. 4 shows the dose dependent inhibition of HIV-1 replication in H9 cells in the presence of GPG-NH$_2$ (white triangles) or G-NH$_2$ (black squares), as measured by p24 levels in cell culture supernatant at day 11 after infection.

In the next series of experiments, it was discovered that glycine amide inhibits HIV replication in a dose dependent manner. HIV infected H9 cells were cultured in the presence of varying concentrations 0.5–20 $\mu$M of glycine amide or GPG-NH$_2$ (positive control) and the amount of p24 present in the culture supernatant was determined at day 11 after infection. The methodology employed was that described in EXAMPLE 2. As shown in FIG. 4, significant inhibition of HIV replication was achieved at concentrations of glycine amide less than 5 $\mu$M. The data also show that 20 $\mu$M glycine amide almost completely inhibited HIV replication. These results clearly indicate that as the concentration of glycine amide was increased the amount of p24 in the supernatant, which indicates the amount of HIV infection or HIV replication, decreased.

In another series of experiments, it was determined that the tripeptide amides GPG-NH$_2$ and ALG-NH$_2$ interfere or inhibit proper budding of HIV. HIV infected cells cultured with GPG-NH$_2$ or ALG-NH$_2$, when viewed by electron microscopy, displayed a unique nodular structure associated with the outer membrane of virus producing cells. These structures were only found in cells treated with GPG-NH$_2$ or ALG-NH$_2$. Most of the treated cells that carried virus particles had these nodular structures (74% with GPG-NH$_2$ treated ACH-2 cells, 65% with GPG-NH$_2$ treated HUT$_{78}$ cells and 56% with ALG-NH$_2$ treated HUT$_{78}$ cells). ACH-2 cells that were treated with 1 mM GPG-NH$_2$ but not stimulated with PMA to produce virus did not show such nodules. Combined treatment of PMA stimulated ACH-2 cells with GPG-NH$_2$ (1 mM) and the protease inhibitor ritonavir (2 $\mu$M) gave no such nodules.

In the latter experiments only budding virus particles of normal appearance and immature virus particles were seen. By tilting, it was shown that the dense nodules were protruding from the outer cell membrane. The size which was approximately 50 nm, was that of the dense, distributed material of the irregular viral core which was an internal reference. Occasionally, such a dense nodular structure was also observed attached to the outer part of viral envelope: 2% (with ACH-2 cells), 4% (with HUT$_{78}$ cells) upon GPG-NH$_2$ treatment and 8% upon ALG-NH$_2$ treatment of HUT$_{78}$ cells.

In immune EM analysis it was shown that the small particles, assembled on the outer membrane, bound gold-labelled anti-p24 antibody. Furthermore, evaluation of TEM results was accomplished by a 3-D computer modeled reconstruction from tilt TEM of HIV-1 from cultures with and without GPG-NH$_2$. These results provide evidence that tripeptide amides inhibit or interfere with viral budding of HIV. The section below describes the use of the small molecules described herein to inhibit replication of viruses other that HIV.

Small Molecules That Inhibit and/or Prevent Viral Replication and Infection

Small molecules that inhibit viral replication include glycine amide and the tripeptide amides AIG-NH$_2$, GFG-NH$_2$, GWG-NH$_2$, FLG-NH$_2$, GYG-NH$_2$, LNF-NH$_2$, APG-NH$_2$, GLG-NH$_2$, and $\alpha$-t-butylglycine-PG-NH$_2$. Peptidomimetics that resemble AIG-NH$_2$, GFG-NH$_2$, GWG-NH$_2$, FLG-NH$_2$, GYG-NH$_2$, APG-NH$_2$, GLG-NH$_2$, and $\alpha$-t-butylglycine-PG-NH$_2$ are also embodiments of the present invention. The small molecules described herein can be used to inhibit capsid assembly and replication of viruses that are members of the arenavirus, rotavirus, orbivirus, retrovirus, papillomavirus, adenovirus, herpesvirus, paramyxovirus, myxovirus, and hepadnavirus families. These molecules can be rapidly screened against these viruses, using the teachings described herein or those that would be apparent to one of skill in the art.

To test the ability of glycine amide and the tripeptide amides AIG-NH$_2$, GFG-NH$_2$, GWG-NH$_2$, FLG-NH$_2$, GYG-NH$_2$, APG-NH$_2$, GLG-NH$_2$, and α-t-butylglycine-PG-NH$_2$ to suppress the growth of mammalian DNA viruses antiviral screening against Herpes Simplex Type 1 (HSV-1) and Herpes Simplex Type 2 (HSV-2) can be performed in tissue culture using human foreskin fibroblast cells, for example. (See e.g., U.S. Pat. No. 6,248,782 to Elford , et al., expressly incorporated by reference in its entirety). In these infectivity assays, a semi-automated CPE-inhibition assay can be used employing HSV-1 E-377 strain and HSV-2 MS strain. Additionally, the ability of tripeptide amides to inhibit cytomegalo virus (CMV) can be determined using a semi-automated CPE inhibition assay and the AD169 strain and for varicellovirus (VZV), a plaque reduction assay using ELLEN strain. Glycine amide and the tripeptide amides can also be screened against Epstein Barr Virus (EBV) in Raji cells (a Burkitt's lymphoma cell line containing 60 EBV genomes/cell) using an immunofluorescence assay with monoclonal antibodies directed against EBV components.

Toxicity can be determined by visual inspection of treated cells, generally stationary cells and a cell proliferation assay can be carried out by determining the presence of rapidly growing cells and either an $EC_{50}$ (concentration required to inhibit viral cytopathogenicity by 50% ) or an $IC_{50}$ (concentration μg/ml) required to inhibit cell proliferation 50% ) can be calculated. Also a Selective Index (S.I.) $IC_{50}/EC_{50}$ can be determined. As above, it is expected that a 100 μM concentration of tripeptide amide or less in these assays would be sufficient to significantly inhibit the replication and/or infectivity of HSV, CMV, VZV, and EBV.

It is preferred that the glycine and tripeptides possess a modulation group (e.g., an amide group) at their carboxy termini (CO—$NH_2$) rather than a carboxyl group (COOH). Other modulation groups at the carboxy terminus can also be used but desirably, the attached modulation groups have the same charge and sterically behave the same as an amide group. (See U.S. Pat. No. 5,627,035 to Vahlne et al., for an assay to compare peptides having differing substituents at the carboxyl terminus, herein incorporated by reference in its entirety). In some embodiments, the addition of an acetyl or methyl group at either end of the small peptide is desirable so as to improve uptake of the small peptide or prevent exo-protease digestion or both. In the following section, several approaches are provided to make biotechnological tools and pharmaceutical compositions comprising the small molecules described herein.

Biotechnological Tools and Pharmaceutical Compositions Comprising Glycine Amide and/or Tripeptide Amides Desirable biotechnological tools or components to prophylactic or therapeutic agents provide the glycine amide or the tripeptide amides in such a form or in such a way that a sufficient affinity for inhibition of a virus, such as HIV-1, is obtained. While a natural monomeric peptide agent (e.g., appearing as discrete units of the peptide agent each carrying only one binding epitope) is sufficient to bind a capsomere protein, such as p24, and/or interfere with capsid assembly and/or inhibit proper viral budding and/or prevent viral infection, such as HIV-1 infection, synthetic ligands or multimeric ligands (e.g., appearing as multiple units of the peptide agent with several binding epitopes) may have far greater ability to bind a capsomere protein, such as p24, and/or interfere with capsid assembly and/or inhibit proper viral budding, and/or prevent viral infection, such as HIV-1 infection. It should be noted that the term "multimeric" refers to the presence of more than one unit of a ligand, for example several individual molecules of glycine amide and/or a tripeptide amide, as distinguished from the term "multimerized" that refers to the presence of more than one tripeptide amide joined as a single discrete unit in tandem.

A multimeric agent (synthetic or natural) that binds a capsomere protein, such as p24, and/or interferes with capsid assembly and/or inhibits proper viral budding and/or inhibits viral infection, such as HIV-1 infection, may be obtained by coupling glycine amide and/or a tripeptide amide to a macromolecular support. The term "support" as used herein includes a carrier, a resin or any macromolecular structure used to attach, immobilize, or stabilize a peptide agent. Solid supports include, but are not limited to, the walls of wells of a reaction tray, test tubes, polystyrene beads, magnetic beads, nitrocellulose strips, membranes, microparticles such as latex particles, sheep (or other animal) red blood cells, artificial cells and others. The term "support" also includes carriers as that term is understood for the preparation of pharmaceuticals.

The macromolecular support can have a hydrophobic surface that interacts with a portion of the peptide agent by hydrophobic non-covalent interaction. The hydrophobic surface of the support can also be a polymer such as plastic or any other polymer in which hydrophobic groups have been linked such as polystyrene, polyethylene or polyvinyl. Alternatively, the peptide agent can be covalently bound to carriers including proteins and oligo/polysaccarides (e.g. cellulose, starch, glycogen, chitosane or aminated sepharose). In these later embodiments, a reactive group on the peptide agent, such as a hydroxy or an amino group, can be used to join to a reactive group on the carrier so as to create the covalent bond. The support can also have a charged surface that interacts with the peptide agent. Additionally, the support can have other reactive groups that can be chemically activated so as to attach a peptide agent. For example, cyanogen bromide activated matrices, epoxy activated matrices, thio and thiopropyl gels, nitrophenyl chloroformate and N-hydroxy succinimide chlorformate linkages, and oxirane acrylic supports are common in the art.

The support can also comprise an inorganic carrier such as silicon oxide material (e.g. silica gel, zeolite, diatomaceous earth or aminated glass) to which the peptide agent is covalently linked through a hydroxy, carboxy or amino group and a reactive group on the carrier. Furthermore, in some embodiments, a liposome or lipid bilayer (natural or synthetic) is contemplated as a support and peptide agents are attached to the membrane surface or are incorporated into the membrane by techniques in liposome engineering. By one approach, liposome multimeric supports comprise a peptide agent that is exposed on the surface of the bilayer and a second domain that anchors the peptide agent to the lipid bilayer. The anchor can be constructed of hydrophobic amino acid residues, resembling known transmembrane domains, or can comprise ceramides that are attached to the first domain by conventional techniques.

Supports or carriers for use in the body, (i.e. for prophylactic or therapeutic applications) are desirably physiological, non-toxic and preferably, non-immunoresponsive. Contemplated carriers for use in the body include poly-L-lysine, poly-D, L-alanine, liposomes, and Chromosorb® (Johns-Manville Products, Denver Colo.). Ligand conjugated Chromosorb® (Synsorb-Pk) has been tested in humans for the prevention of hemolytic-uremic syndrome and was reported as not presenting adverse reactions. (Armstrong et al. *J. Infectious Diseases*, 171:1042–1045 (1995)). For some embodiments, the administration of a "naked" carrier (i.e., lacking an attached peptide agent) that has the capacity to attach a peptide agent in the body of a subject is contemplated. By this approach, a "prodrug-type" therapy is envisioned in which the naked carrier is administered separately from the peptide agent and, once both are in the body of the subject, the carrier and the peptide agent are assembled into a multimeric complex.

Additionally, prodrugs, which are compounds that break down in the body (e.g., a human) to yield an active ingredient of the invention (e.g., glycine amide or a tripeptide selected from the group consisting of AIG-NH$_2$, GFG-NH$_2$, GWG-NH$_2$, FLG-NH$_2$, GYG-NH$_2$, APG-NH$_2$, GLG-NH$_2$) are embodiments. It is contemplated that several molecules can be designed such that upon introduction to a human, they undergo proteolysis or degradation to achieve glycine amide or a tripeptide selected from the group consisting of AIG-NH$_2$, GFG-NH$_2$, GWG-NH$_2$, FLG-NH$_2$, GYG-NH$_2$, APG-NH$_2$, GLG-NH$_2$. Because these prodrug molecules break down to the active ingredients glycine amide or a tripeptide selected from the group consisting of AIG-NH$_2$, GFG-NH$_2$, GWG-NH$_2$, FLG-NH$_2$, GYG-NH$_2$, APG-NH$_2$, GLG-NH$_2$ they are equivalent to these molecules.

The insertion of linkers, such as λ linkers, of an appropriate length between the peptide agent and the support are also contemplated so as to encourage greater flexibility of the peptide agent and thereby overcome any steric hindrance that may be presented by the support. The determination of an appropriate length of linker that allows for optimal binding to a capsomere protein, such as p24, and/or interference with capsid assembly and/or inhibition of viral infection, such as HIV infection, can be determined by screening the peptide agents with varying linkers in the assays detailed in the present disclosure.

Another aspect of the invention includes a composite support comprising more than one type of peptide agent. A "composite support" may be a carrier, a resin, or any macromolecular structure used to attach or immobilize two or more different peptide agents that bind to a capsomere protein, such as p24, and/or interfere with capsid assembly and/or inhibit proper viral budding and/or inhibit viral infection, such as HIV infection. In some embodiments, a liposome or lipid bilayer (natural or synthetic) is contemplated for use in constructing a composite support and peptide agents are attached to the membrane surface or are incorporated into the membrane using techniques in liposome engineering.

The insertion of linkers, such as λ linkers, of an appropriate length between the peptide agent and the support is also contemplated so as to encourage greater flexibility in the molecule and thereby overcome any steric hindrance that may occur. The determination of an appropriate length of linker that allows for optimal binding to a capsomere protein, such as p24, and/or interference with capsid assembly and/or inhibition of proper viral budding and/or inhibition of viral infection, such as HIV infection, can be determined by screening the ligands with varying linkers in the assays detailed in the present disclosure.

In other embodiments, the multimeric and composite supports discussed above can have attached multimerized ligands so as to create a "multimerized-multimeric support" and a "multimerized-composite support", respectively. A multimerized ligand can be obtained, for example, by coupling two or more peptide agents in tandem using conventional techniques in molecular biology. The multimerized form of the ligand can be advantageous for many applications because of the ability to obtain an agent with a better ability to bind to a capsomere protein, such as p24, and/or interfere with capsid assembly and/or inhibit viral infection, such as HIV or SIV infection. Further, the incorporation of linkers or spacers, such as flexible λ linkers, between the individual domains that make-up the multimerized agent is another embodiment. The insertion of λ linkers of an appropriate length between protein binding domains, for example, can encourage greater flexibility in the molecule and can overcome steric hindrance. Similarly, the insertion of linkers between the multimerized ligand and the support can encourage greater flexibility and limit steric hindrance presented by the support. The determination of an appropriate length of linker that allows for optimal binding to p24 and/or interference with capsid assembly and/or inhibition of proper viral budding and/or inhibition of HIV infection, can be determined by screening the ligands with varying linkers in the assays detailed in this disclosure.

In preferred embodiments, the various types of supports discussed above are created using glycine amide or the tripeptide amides AIG-$NH_2$, GFG-$NH_2$, GWG-$NH_2$, FLG-$NH_2$, GYG-$NH_2$, APG-$NH_2$, GLG-$NH_2$, and α-t-butylglycine-PG-$NH_2$. The multimeric supports, composite supports, multimerized-multimeric supports, or multimerized-composite supports, collectively referred to as "support-bound agents", are also preferably constructed using glycine amide or the tripeptide amides AIG-$NH_2$, GFG-$NH_2$, GWG-$NH_2$, FLG-$NH_2$, GYG-$NH_2$, APG-$NH_2$, GLG-$NH_2$, and α-t-butylglycine-PG-$NH_2$.

The monomeric and multimeric peptide agents described herein are suitable for use as a biotechnological tool to study the interaction of glycine amide or tripeptide amides with capsid proteins and also as medicaments for the treatment of subjects already infected with a virus, such as HIV, or as a preventive measure to avoid viral infections, such as HIV infection. Although anyone could be treated with glycine amide or the tripeptide amides as a prophylactic, the most suitable subjects are people at risk for viral infection. Such subjects include, but are not limited to, the elderly, the chronically ill, homosexuals, prostitutes, intravenous drug users, hemophiliacs, children, and those in the medical profession who have contact with patients or biological samples. The following section discusses methods of making and using the medicaments described herein.

Methods of Making and Using Medicaments Comprising Glycine Amide and/or Tripeptide Amides Methods of making and using medicaments comprising glycine amide and/or the tripeptide amides disclosed herein are also embodiments of the present invention. The peptide agents described herein can be processed in accordance with conventional methods of galenic pharmacy to produce medicinal agents for administration to patients, e.g., mammals including humans. The peptide agents can be incorporated into a pharmaceutical product with and without modification. Further, the manufacture of pharmaceuticals or therapeutic agents that deliver the peptide agent by several routes is included within the scope of the present invention.

The compounds described herein can be employed in admixture with conventional excipients, i.e., pharmaceutically acceptable organic or inorganic carrier substances suitable for parenteral, enteral (e.g., oral) or topical application that do not deleteriously react with the peptide agents. Suitable pharmaceutically acceptable carriers include, but are not limited to, water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

In some embodiments, medicaments comprising glycine amide and/or tripeptide amides are formulated with or administered in conjunction with other agents that inhibit viral infections, such as HIV infection, so as to achieve a better viral response. At present four different classes of drugs are in clinical use in the antiviral treatment of HIV-1 infection in humans. These are (i) nucleoside analogue reverse transcriptase inhibitors (NRTIs), such as zidovudine, lamivudine, stavudine, didanosine, abacavir, and zalcitabine; (ii) nucleotide analogue reverse transcriptase inhibitors, such as adetovir and pivaxir; (iii) non-nucleoside reverse transcriptase inhibitors (NNRTIs), such as efavirenz, nevirapine, and delavirdine; and (iv) protease inhibitors, such as indinavir, nelfinavir, ritonavir, saquinavir and amprenavir. By simultaneously using two, three, or four different classes of drugs in conjunction with administration of the peptide agents, HIV is less likely to develop resistance, since it is less probable that multiple mutations that overcome the different classes of drugs and the peptide agents will appear in the same virus particle.

It is thus preferred that medicaments comprising peptide agents (e.g., glycine amide or a tripeptide amide selected from the group consisting of AIG-NH$_2$, GFG-NH$_2$, GWG-NH$_2$, FLG-NH$_2$, GYG-NH$_2$, APG-NH$_2$, GLG-NH$_2$, and α-t-butylglycine-PG-NH$_2$) be formulated with or given in combination with nucleoside analogue reverse transcriptase inhibitors, nucleotide analogue reverse transcriptase inhibitors, non-nucleoside reverse transcriptase inhibitors, and protease inhibitors at doses and by methods known to those of skill in the art. Medicaments comprising the peptide agents and nucleoside analogue reverse transcriptase inhibitors, nucleotide analogue reverse transcriptase inhibitors, non-nucleoside reverse transcriptase inhibitors, and protease inhibitors can be formulated to contain other ingredients to aid in delivery, retention, or stability of the glycine amide and/or the tripeptide amide.

The effective dose and method of administration of a particular peptide agents formulation can vary based on the individual patient and the stage of the disease, as well as other factors known to those of skill in the art. Therapeutic efficacy and toxicity of such compounds can be determined by standard pharmaceutical procedures in cell cultures or experimental animals, e.g., ED$_{50}$ and LD$_{50}$ (the dose lethal to 50% of the population). The dose ratio of toxic to therapeutic effects is the therapeutic index, and it can be expressed as the ratio, LD$_{50}$/ED$_{50}$. Pharmaceutical compositions that exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors that may be taken into account include the severity of the disease state, age, weight and gender of the patient; diet, time and frequency of administration, drug combination(s), reaction sensitivities, and tolerance/response to therapy. Short acting pharmaceutical compositions are administered daily whereas long acting pharmaceutical compositions are administered every 2, 3 to 4 days, every week, or once every two weeks. Depending on half-life and clearance rate of the particular formulation, the pharmaceutical compositions of the invention are administered once, twice, three, four, five, six, seven, eight, nine, ten or more times per day.

Normal dosage amounts may vary from approximately 1 to 100,000 micrograms, up to a total dose of about 20 grams, depending upon the route of administration. Desirable dosages include 250 µg, 500 µg, 1 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1 g, 1.1 g, 1.2 g, 1.3 g, 1.4 g, 1.5 g, 1.6 g, 1.7 g, 1.8 g, 1.9 g, 2 g, 3 g, 4 g, 5, 6 g, 7 g, 8 g, 9 g, 10 g, 11 g, 12 g, 13 g, 14 g, 15 g, 16 g, 17 g, 18 g, 19 g, and 20 g. Additionally, the concentrations of the peptide agents can be quite high in embodiments that administer the agents in a topical form. Molar concentrations of peptide agents can be used with some embodiments. Desirable concentrations for topical administration and/or for coating medical equipment range from 100 µM to 800 mM. Preferable concentrations for these embodiments range from 500 µM to 500 mM. For example, preferred concentrations for use in topical applications and/or for coating medical equipment include 500 µM, 550 µM, 600 µM, 650 µM, 700 µM, 750 µM, 800 µM, 850 µM, 900µM, 1 mM, 5 mM, 10 mM, 15 mM, 20 mM, 25 mM, 30 mM, 35 mM, 40 mM, 45 mM, 50 mM, 60 mM, 70 mM, 80 mM, 90 mM, 100 mM, 120 mM, 130 mM, 140 mM, 150 mM, 160 mM, 170 mM, 180 mM, 190 mM, 200 mM, 300 mM, 325 mM, 350 mM, 375 mM, 400 mM, 425 mM, 450 mM, 475 mM, and 500 mM. Guidance as to particular dosages and methods of delivery is provided in the literature and below. (See e.g., U.S. Pat. Nos. 4,657,760; 5,206,344; or 5,225,212, herein expressly incorporated by reference in their entireties).

More specifically, the dosage of the peptide agents described herein is one that provides sufficient peptide agent to attain a desirable effect including binding of a capsomere protein, such as p24, and/or interference with capsid assembly and/or inhibition of proper viral budding and/or inhibition of viral infection, such as HIV infection. Accordingly, the dose of peptide agent preferably produces a tissue or blood concentration or both from approximately 0.1 nM to 500 mM. Desirable doses produce a tissue or blood concentration or both of about 0.1 nM to 800 µM. Preferable doses produce a tissue or blood concentration of greater than about 10 nM to about 300 µM. Preferable doses are, for example, the amount of molecule required to achieve a tissue or blood concentration or both of 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM, 100 nM, 200 nM, 300 nM, 400 nM, 500 nM, 600 nM, 700 nM, 800 nM, 900 nM, 1 µM, 10 µM, 50 µM, 100 µM, 200 µM, and 300 µM. Although doses that produce a tissue concentration of greater than 800 µM are not preferred, they can be used with some embodiments. A constant infusion of the glycine amide and/or tripeptide amide can also be provided so as to maintain a stable concentration in the tissues as measured by blood levels.

Routes of administration of the peptide agents include, but are not limited to, topical, transdermal, parenteral, gastrointestinal, transbronchial, and transalveolar. Topical administration is accomplished via a topically applied cream, gel, rinse, etc. containing a tripeptide amide and/or glycine amide. Transdermal administration is accomplished by application of a cream, rinse, gel, etc. capable of allowing the peptide agent to penetrate the skin and enter the blood stream. Parenteral routes of administration include, but are not limited to, electrical or direct injection such as direct injection into a central venous line, intravenous, intramuscular, intraperitoneal or subcutaneous injection. Gastrointestinal routes of administration include, but are not limited to, ingestion and rectal. Transbronchial and transalveolar routes of administration include, but are not limited to, inhalation, either via the mouth or intranasally.

Compositions of peptide agents containing compounds suitable for topical application include, but are not limited to, physiologically acceptable implants, ointments, creams, rinses, and gels. Any liquid, gel, or solid pharmaceutically acceptable base in which the peptides are at least minimally soluble is suitable for topical use in the present invention. Compositions for topical application are particularly useful during sexual intercourse to prevent transmission of HIV. Suitable compositions for such use include, but are not limited to, vaginal or anal suppositories, creams, and douches.

Compositions of the peptide agents suitable for transdermal administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference and are well known in the art. Examples of suitable transdermal devices are described, for instance, in U.S. Pat. No. 4,818, 540, issued Apr. 4, 1989 to Chinen, et al., hereby incorporated by reference in its entirety.

Compositions of the peptide agents suitable for parenteral administration include, but are not limited to, pharmaceutically acceptable sterile isotonic solutions. Such solutions include, but are not limited to, saline and phosphate buffered saline for injection into a central venous line, intravenous, intramuscular, intraperitoneal, or subcutaneous injection of the peptide agents.

Compositions of the peptide agents suitable for transbronchial and transalveolar administration include, but are not limited to, various types of aerosols for inhalation. For instance, pentamidine is administered intranasally via aerosol to AIDS patients to prevent pneumonia caused by *pneumocystis carinii*. Devices suitable for transbronchial and transalveolar administration of the peptides, including but not limited to atomizers and vaporizers, are also included within the scope of the present invention. Many forms of currently available atomizers and vaporizers can be readily adapted to deliver peptide agents.

Compositions of the peptide agents suitable for gastrointestinal administration include, but not limited to, pharmaceutically acceptable powders, pills, sachets, or liquids for ingestion and suppositories for rectal administration. Due to the most common routes of HIV infection and the ease of use, gastrointestinal administration, particularly oral, is the preferred embodiment of the present invention. Five-hundred milligram capsules having a tripeptide amide have been prepared and were found to be stable for a minimum of 12 months when stored at 4° C. Since small peptides apparently evade degradation by the patient's digestive system, they are ideal for oral administration.

The peptide agents are also suitable for use in situations where prevention of HIV infection is important. For instances, medical personnel are constantly exposed to patients who may be HIV positive and whose secretions and body fluids contain the HIV virus. Further, the peptide agents can be formulated into antiviral compositions for use during sexual intercourse so as to prevent transmission of HIV. Such compositions are known in the art and also described in the international application published under the PCT publication number WO90/04390 on May 3, 1990 to Modak et al., which is incorporated herein by reference in its entirety.

Embodiments of the invention also include a coating for medical equipment such as gloves, sheets, and work surfaces that protects against viral transmission. Alternatively, the peptide agents can be impregnated into a polymeric medical device. Particularly preferred are coatings for medical gloves and condoms. Coatings suitable for use in medical devices can be provided by a powder containing the peptides or by polymeric coating into which the peptide agents are suspended. Suitable polymeric materials for coatings or devices are those that are physiologically acceptable and through which a therapeutically effective amount of the peptide agent can diffuse. Suitable polymers include, but are not limited to, polyurethane, polymethacrylate, polyamide, polyester, polyethylene, polypropylene, polystyrene, polytetrafluoroethylene, polyvinyl-chloride, cellulose acetate, silicone elastomers, collagen, silk, etc. Such coatings are described, for instance, in U.S. Pat. No. 4,612,337, issued Sep. 16, 1986 to Fox et al., which is incorporated herein by reference in its entirety.

Accordingly, methods of making a medicament that inhibits viral replication, specifically, HIV, involve providing glycine amide and/or a tripeptide amide selected from the group consisting of $AIG-NH_2$, $GFG-NH_2$, $GWG-NH_2$, $FLG-NH_2$, $GYG-NH_2$, $APG-NH_2$, $GLG-NH_2$, and $\alpha$-t-butylglycine-$PG-NH_2$, and formulating said medicament for delivery to a subject, including a human, as described above.

Methods of identification of peptide agents that inhibit viral replication, specifically HIV replication, are also provided. By one method, for example, a peptide agent for incorporation into an anti-viral pharmaceutical is identified by contacting a plurality of cells infected with a virus with an effective amount of a peptide agent analyzing the virus for incomplete capsid formation and/or impaired viral budding, and selecting the peptide agent that induces incomplete capsid formation. This method can involve microscopic analysis and the virus can be selected from the group consisting of HIV-1, HIV-2, and SIV. Further, the peptide agent identified can be selected from the group consisting of glycine amide, a tripeptide amide, and a peptidomimetic resembling a tripeptide amide. For example, the peptide agent above can be selected from the group consisting of glycine amide, $AIG-NH_2$, $GFG-NH_2$, $GWG-NH_2$, $FLG-NH_2$, $GYG-NH_2$, $APG-NH_2$, $GLG-NH_2$, and $\alpha$-t-butylglycine-$PG-NH_2$.

In another embodiment, a method of identifying a peptide agent that binds to a viral protein is provided. Some aspects of this method involve providing a viral protein, contacting the viral protein with an effective amount of a peptide agent, and detecting the formation of a complex comprising the viral protein and the peptide agent. Preferably, the viral protein is from a virus selected from the group consisting of HIV-1, HIV-2, and SIV. The detection step can be accomplished by performing a binding assay (e.g., a p24 binding assay involving dialysis, capillary electrophoresis, computer modeling, or crystallography).

A method of identifying a peptide agent that binds to a viral protein using dialysis can be performed, as follows. Approximately 50 μl of 10 μM solutions of recombinant protein p24, recombinant gp120, or BSA are placed in a 10 kD cut-off dialysis cassette (Slide-A-Lyzer from Pierce) and are dialyzed against 500 ml of buffer containing 150 mM NaCl, 50 mM Tris-HCl, pH 7.4, and 27.5 μM $^{14}$C labeled tripeptide amide at 4° C. for 2 days. Radioactivity can then be quantified in a Rackbeta 1218 (LKB Wallace) after mixing 10 μl or 5 μl of the proteins in ReadySafe (Beckman).

Another method of identifying a peptide agent that binds to a viral protein using dialysis can be performed as follows. A piece of fused silica tubing (inner diameter 50 μm) is cut to a length of 23 cm (length to the detector 18.5 cm) and coated prior to use with 5% (w/v) linear polyacrylamide (Hjertén, S. *J. Chromatogr.* 347, 191–198 (1985), expressly incorporated by reference in its entirety) in order to suppress the electroendosmotic flow and to avoid unwanted adsorption of proteins onto the capillary wall. A 0.01 M sodium phosphate solution is used as buffer in the pH range 6.8–8.2. The tripeptide amides are dissolved in the buffer at a relatively high concentration (0.5 mg/ml) because of their low UV-absorbance. A stock solution of p24 is diluted ten-fold with the running buffer to a final concentration of 50 μg/ml. The capillary is filled with the buffer. The protein is injected by pressure (50 psi per second) and then the tripeptide sample (1 psi per second). Since the electrophoretic migration velocity of the peptide is higher than that of the protein, the peptide molecules will move through the protein zone (Hjertén, S. Analysis and purification of cells with the free zone electrophoresis equipment. In *Cell Separation Methods*, Loemendal, H., editor. Elsevier/North-Holland Biomedical Press (1977), expressly incorporated by reference in its entirety). Spectra can be recorded over the whole UV range (195–360 nm with 5 nm frequency) for on tube identification of the peaks. An interaction between the viral protein and the peptide will be revealed as an increase in migration time of the peptide compared to that in the absence of the protein.

In some embodiments, the peptide agent is selected from the group consisting of glycine amide, AIG-NH$_2$, GFG-NH$_2$, GWG-NH$_2$, FLG-NH$_2$, GYG-NH$_2$, APG-NH$_2$, GLG-NH$_2$, and α-t-butylglycine-PG-NH$_2$. Additionally, a method of making a pharmaceutical is provided in which the peptide agent identified by the methods above are incorporated in a pharmaceutical.

Another approach to making a pharmaceutical involves administering to a cell an effective amount of glycine amide and/or a tripeptide amide, described above, detecting an inhibition of viral replication in the cell, and incorporating the tripeptide amide that causes inhibition of viral replication into the pharmaceutical. This method can involve the use of glycine amide or a tripeptide amide selected from the group consisting of AIG-NH$_2$, GFG-NH$_2$, GWG-NH$_2$, FLG-NH$_2$, GYG-NH$_2$, APG-NH$_2$, GLG-NH$_2$, and α-t-butylglycine-PG-NH$_2$. Further, the method above can be supplemented with administration of an antiviral compound selected from the group consisting of nucleoside analogue reverse transcriptase inhibitors, nucleotide analogue reverse transcriptase inhibitors, non-nucleoside reverse transcriptase inhibitors, and protease inhibitors into the pharmaceutical. Additionally, the method above can be supplemented by incorporating a carrier into the pharmaceutical.

Although the peptide agents described herein can be used as research tools to analyze the interaction of glycine amide and/or a tripeptide amide with a protein, desirably they are used to inhibit viral replication and/or infection, preferably, HIV replication and infection in a subject. By one method, for example, a subject at risk of becoming infected by HIV or who is already infected with HIV is identified and said subject is provided glycine amide and/or a tripeptide amide selected from the group consisting of AIG-NH$_2$, GFG-NH$_2$, GWG-NH$_2$, FLG-NH$_2$, GYG-NH$_2$, APG-NH$_2$, GLG-NH$_2$, and α-t-butylglycine-PG-NH$_2$. By an additional method, a subject is provided glycine amide and/or a tripeptide amide selected from the group consisting of AIG-NH$_2$, GFG-NH$_2$, GWG-NH$_2$, FLG-NH$_2$, GYG-NH$_2$, APG-NH$_2$, GLG-NH$_2$, and α-t-butylglycine-PG-NH$_2$ and the effect on viral replication or infection, preferably HIV replication or infection, is determined (e.g., by analyzing the amount of p24 or reverse transcriptase activity in a sample).

The methods above can be supplemented with administration of an antiviral treatment selected from the group consisting of nucleoside analogue reverse transcriptase inhibitors, nucleotide analogue reverse transcriptase inhibitors, non-nucleoside reverse transcriptase inhibitors, and protease inhibitors. Further, the tripeptide amide used in these methods can be joined to a support or can be administered in a pharmaceutical comprising a pharmaceutically acceptable carrier.

While the present invention has been described in some detail for purposes of clarity and understanding, one skilled in the art will appreciate that various changes in form and detail can be made without departing from the true scope of the invention. All figures and tables, as well as patents, applications, and publications referred to above are hereby expressly incorporated by reference in their entireties.

What is claimed is:

1. An antiviral composition for human administration comprising monopeptidic glycine amide and a compound that inhibits replication of HIV in the presence of monopeptidic glycine amide.

2. The antiviral composition of claim 1, wherein said antiviral composition is formulated for oral administration.

3. The antiviral composition of claim 1, wherein the amount of glycine amide is 250 μg or more.

4. The antiviral composition of claim 1, wherein said compound that inhibits replication of HIV in the presence of monopeptidic glycine amide is a peptide.

5. The antiviral composition of claim 4, wherein said peptide is selected from the group consisting of AIG-NH$_2$, GFG-NH$_2$, GWG-NH$_2$, FLG-NH$_2$, GYG-NH$_2$, APG-NH$_2$, GLG-NH$_2$, and a-t-butylglycine-PG-NH$_2$.

6. The antiviral composition of claim 4, wherein said antiviral composition is formulated for oral administration.

7. The antiviral composition of claim 4, wherein said antiviral composition comprises 250 μg glycine amide.

8. The antiviral composition of claim 4, wherein said antiviral composition comprises 1 mg glycine amide.

9. The antiviral composition of claim 4, wherein said antiviral composition comprises 50 mg glycine amide.

10. The antiviral composition of claim 4, wherein said antiviral composition comprises 100 mg glycine amide.

11. The antiviral composition of claim 4, wherein said antiviral composition comprises 300 mg glycine amide.

12. The antiviral composition of claim 1, wherein said compound that inhibits replication of HIV in the presence of monopeptidic glycine amide is selected from the group consisting of nucleoside analogue reverse transcriptase inhibitors, nucleotide analogue reverse transcriptase inhibitors, non-nucleoside reverse transcriptase inhibitors, and protease inhibitors.

13. The antiviral composition of claim 12, wherein said compound that inhibits replication of HIV in the presence of monopeptidic glycine amide is selected from the group consisting of azidothymidine (AZT), zidovudine, lamivudine, stavudine, didanosine, abacavir, zalcitabine, adetovir, pivaxir, efavirenz, nevirapine, delavirdine, indinavir, nelfinavir, ritonavir, saquinavir, and amprenavir.

14. The antiviral composition of claim 12, wherein said antiviral composition is formulated for oral administration.

15. The antiviral composition of claim 12, wherein the amount of glycine amide is 250 µg or more.

16. A pill comprising monopeptidic glycine amide formulated for human administration in unit dosage form.

17. An oral suspension comprising 1 mg monopeptidic glycine amide and a flavoring, formulated for human administration.

18. A suppository comprising monopeptidic glycine amide formulated for human administration.

19. A transdermal composition comprising monopeptidic glycinamide formulated for human administration.

* * * * *

UNITED STATES PATENT AND TRADEMARK OFFICE
CERTIFICATE OF CORRECTION

PATENT NO. : 7,012,129 B2
APPLICATION NO. : 10/406012
DATED : March 14, 2006
INVENTOR(S) : Anders Vahlne et al.

It is certified that error appears in the above-identified patent and that said Letters Patent is hereby corrected as shown below:

On the title page, item [56]:

Page 3, column 2, line 17, delete "Vahine," and insert -- Vahlne, --

Drawings, Figure 1, delete "infected contro" and insert -- infected control -- column 2, line 11, after "some" delete "SWV" and insert -- SIV -- column 3, lines 29-30, delete "Imnmunodeficiency" and insert -- Immunodeficiency -- column 5, line 16, delete "SWV." and insert -- SIV. -- column 5, line 37, delete "GFG-NF$_2$" and insert -- GFG-NH$_2$ -- column 6, line 1, delete "capture-enzyme-linked" and insert -- capture enzyme-linked -- column 6, line 24, Delete "EMBODIMENT" and insert -- EMBODIMENTS --

(Table 1), column 7, line 30, delete "fenylalanyl" and insert -- phenylalanyl -- column 8, line 39, delete "syntheses." and insert -- synthesis. -- column 24, line 12, delete "OPA-NH$_2$," and insert -- GPA-NH$_2$, --

Column 13, Tables 3 and 4, the chemical formulas, delete "NH2" and insert -- NH$_2$ --

Signed and Sealed this

Third Day of October, 2006

JON W. DUDAS
*Director of the United States Patent and Trademark Office*